(12) United States Patent
Cheng et al.

(10) Patent No.: US 9,853,221 B2
(45) Date of Patent: Dec. 26, 2017

(54) COMPOUND, EMITTING LAYER OF ORGANIC LIGHT EMITTING DIODE AND ORGANIC LIGHT EMITTING DIODE DEVICE

(71) Applicant: NATIONAL TSING HUA UNIVERSITY, Hsinchu (TW)

(72) Inventors: Chien-Hong Cheng, Hsinchu (TW); Pachaiyappan Rajamalli, Hsinchu (TW); Natarajan Senthilkumar, Hsinchu (TW); Parthasarathy Gandeepan, Hsinchu (TW); Min-Hsien Chen, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/232,822

(22) Filed: Aug. 10, 2016

(65) Prior Publication Data
US 2017/0317292 A1  Nov. 2, 2017

(30) Foreign Application Priority Data

Apr. 27, 2016 (TW) .............................. 105113100 A

(51) Int. Cl.
| | | |
|---|---|---|
| *H01L 51/54* | (2006.01) | |
| *C09K 11/06* | (2006.01) | |
| *H01L 51/00* | (2006.01) | |
| *C09K 11/02* | (2006.01) | |
| *C07D 401/14* | (2006.01) | |
| *C07D 401/10* | (2006.01) | |
| *H01L 51/50* | (2006.01) | |
| *H01L 51/52* | (2006.01) | |

(52) U.S. Cl.
CPC ........ *H01L 51/0067* (2013.01); *C07D 401/10* (2013.01); *C07D 401/14* (2013.01); *C09K 11/025* (2013.01); *C09K 11/06* (2013.01); *H01L 51/005* (2013.01); *H01L 51/0072* (2013.01); *H01L 51/0074* (2013.01); *C09K 2211/1007* (2013.01); *C09K 2211/1029* (2013.01); *H01L 51/5016* (2013.01); *H01L 51/5056* (2013.01); *H01L 51/5072* (2013.01); *H01L 51/5096* (2013.01); *H01L 51/5206* (2013.01); *H01L 2251/552* (2013.01)

(58) Field of Classification Search
CPC ....... C09K 11/00; C09K 11/025; C09K 11/06; C09K 2211/00; C09K 2211/10; C09K 2211/1003; C09K 2211/1007; C09K 2211/1029; C07D 401/00; C07D 401/02; C07D 401/10; C07D 401/14; C07D 209/86; C07D 221/00; H01L 2251/00; H01L 2251/55; H01L 2251/552; H01L 51/0032; H01L 51/005; H01L 51/0051; H01L 51/0062; H01L 51/0067; H01L 51/0071; H01L 51/0072; H01L 51/0074; H01L 51/50; H01L 51/5012; H01L 51/5016; H01L 51/5056; H01L 51/5072; H01L 51/5096; H01L 51/5206
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

FOREIGN PATENT DOCUMENTS

| | | |
|---|---|---|
| CN | 105153153 A | 12/2015 |
| TW | 201002726 A | 1/2010 |
| WO | WO-2014168101 A1 * | 10/2014 ......... H01L 51/0072 |

OTHER PUBLICATIONS

Pachaiyappan Rajamalli et al., "A New Molecular Design Based on Thermally Activated Delayed Fluorescence for Highly Efficient Organic Light Emitting Diodes", Journal of the American Chemical Society, Jan. 20, 2016, vol. 138, issue 2, pp. 628-634, published by ACS Publications, Unites States.
Pachaiyappan Rajamalli et al., "A thermally activated delayed blue fluorescent emitter with reversible externally unable emission", Journal of Materials Chemistry C, Feb. 7, 2016, issue 5, pp. 900-904, published by Royal Society of Chemistry, England.

* cited by examiner

*Primary Examiner* — Andrew K Bohaty
(74) *Attorney, Agent, or Firm* — CKC & Partners Co., Ltd.

(57) ABSTRACT

The present disclosure relates to a compound including a structure of Formula (I), and the use of the compound as a dopant in an emitting layer of an organic light emitting diode. The present disclosure also relates to an emitting layer of an organic light emitting diode and an organic light emitting diode device.

11 Claims, 27 Drawing Sheets

COMPOUND, EMITTING LAYER OF ORGANIC LIGHT EMITTING DIODE AND ORGANIC LIGHT EMITTING DIODE DEVICE

RELATED APPLICATIONS

This application claims priority to Taiwan Application Serial Number 105113100, filed Apr. 27, 2016, which is herein incorporated by reference.

BACKGROUND

Technical Field

The present disclosure relates to a compound, an emitting layer of an organic light emitting diode (OLED) and an OLED device. More particularly, the present disclosure relates to a compound can be used as a dopant of an emitting layer of an OLED, and an emitting layer of an OLED and an OLED device having the same.

DESCRIPTION OF RELATED ART

An OLED refers to a component having an emitting layer made of organic molecules, which can emit light in response to a driving voltage. Comparing to a liquid crystal display, the OLED has advantages of lighter weight, wider view angle, higher contrast ratio, lower power consumption, faster response times, high luminous efficiency, facile color tuning of emitters, access to flexible panels. Accordingly, the OLED draws lots of attention from the relevant industry.

The earliest OLED adopts fluorescence materials, in which excitons can transition from a singlet excited state to a singlet ground state and release energy in the form of fluorescence. However, the internal quantum efficiency (IQE) of fluorescence materials can only reach to 25%, and the rest of 75% is lost in the non-radiative form of heat. Accordingly, the efficiency of the fluorescence material is poor.

Then the OLED adopting phosphorescence materials is provided, in which noble metals, such as Ir, Pt, Os and Ru, are introduced into the emitting layer to form complexes with organic molecules so as to generate the effect of spin-orbital coupling. As a result, the fluorescence generated from the transition from the singlet excited state to the singlet ground state and the phosphorescence generated from the transition from a triplet excited state to the singlet ground state can be obtained at the same time, so that the IQE of phosphorescence materials can reach to 100%. Introducing the noble metals into the emitting layer increases the efficiency of the OLED significantly. However, the noble metals are expansive, so that the cost of the phosphorescence materials remains stubbornly high. Furthermore, blue OLEDs still cannot be manufactured with the phosphorescence materials.

Thermal activated delayed fluorescence (TADF) materials are the third generation organic light emitting materials, which are developed after the fluorescence materials and the phosphorescence materials. The energy gap of the singlet excited state and the triplet excited state ($\Delta E_{ST}$) of the TADF materials is small, which allows excitons to transition from the triplet excited state to the singlet excited state through reverse intersystem crossing (RISC). Therefore, the TADF materials can take advantage of the excitons in singlet excited state and triplet excited state releasing energy in radiative form (fluorescence and delayed fluorescence), which enables the IQE of the TADF materials to reach to 100%. The TADF materials are featured with high efficiency, low cost (due to no use of noble metals) and can provide a wide light color tenability (capable of manufacturing blue OLEDs). Accordingly, the TADF materials have received lots of attention.

However, the OLEDs made of the TADF materials are hardly to provide an external quantum efficiency (EQE) comparable to that of the phosphorescence materials. Researches show that the molecular structure of the TADF material is critical to the performance of the OLEDs. For example, it is realized that in molecules with a small overlap between their highest occupied molecular orbital (HOMO) bearing electron donating groups and lowest unoccupied molecular orbital (LUMO) bearing electron accepting groups can increase the TADF property. Furthermore, by increasing the twist angle between a plane of the electron donating group and a plane of the electron accepting group can lower the $\Delta E_{ST}$, which can increase the probability of RISC. However, an excessive twist angle may inhibit the radiative decay of the transition from the singlet excited state to the singlet ground state, which reduces the luminous efficiency.

To sum up, how to improve the molecular structure of the TADF materials, in which the electron donating groups and the electron accepting groups are properly arranged, so as to provide the OLEDs with excellent efficiency is the goal of the relevant industry and academia.

SUMMARY

According to one aspect of the present disclosure, a compound includes a structure of Formula (I):

In Formula (I), $A^1$ is a pyridyl group, $A^2$ is a phenyl group or a pyridyl group, and hydrogens of the $A^1$ are both unsubstituted or substituted by a structure of Formula (i), Formula (ii) or Formula (iii), and at least one of hydrogens of the $A^2$ is substituted by the structure of Formula (i), Formula (ii) or Formula (iii):

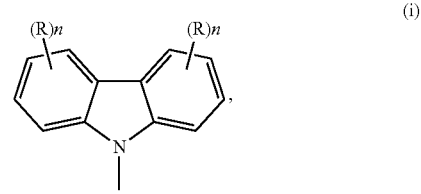

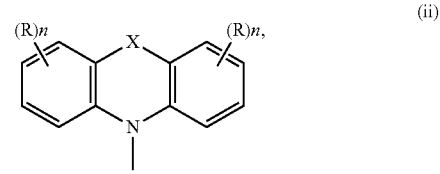

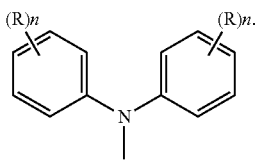

In Formula (i) to Formula (iii), n is independently an integer of 0 to 4, R is independently a monovalent group having 1 to 60 carbon atoms, X is $-NR^{14}-$, $-S-$ or $-CR^{15}R^{16}-$, and $R^{14}$, $R^{15}$ and $R^{16}$ are independently $-H$, an alkyl group or an aryl group.

According to another aspect of the present disclosure, an emitting layer of an OLED includes a dopant, the dopant includes a structure of Formula (I):

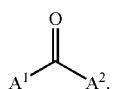

In Formula (I), $A^1$ is a pyridyl group, $A^2$ is a phenyl group or a pyridyl group, and hydrogens of the $A^1$ are both unsubstituted or substituted by a structure of Formula (i), Formula (ii) or Formula (iii), and at least one of hydrogens of the $A^2$ is substituted by the structure of Formula (i), Formula (ii) or Formula (iii):

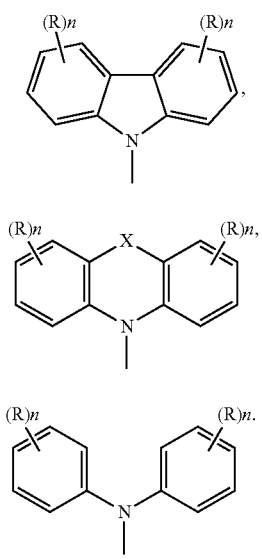

In Formula (i) to Formula (iii), n is independently an integer of 0 to 4, R is independently a monovalent group having 1 to 60 carbon atoms, X is $-NR^{14}-$, $-S-$ or $-CR^{15}R^{16}-$, and $R^{14}$, $R^{15}$ and $R^{16}$ are independently $-H$, an alkyl group or an aryl group.

According to yet another aspect of the present disclosure, an OLED device includes the aforementioned emitting layer of the OLED.

BRIEF DESCRIPTION OF THE DRAWINGS

The present disclosure can be more fully understood by reading the following detailed description of the embodiment, with reference made to the accompanying drawings as follows.

DETAILED DESCRIPTION

Compound

Figure 1:
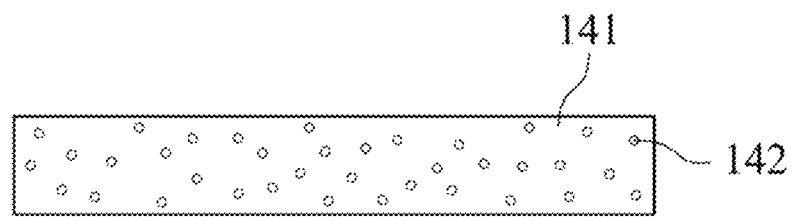
FIG. 1 is a schematic cross-sectional view illustrating an emitting layer of an OLED according to one embodiment of the present disclosure.

A compound includes a structure of Formula (I):

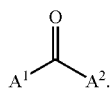
(I)

In Formula (I), $A^1$ is a pyridyl group, $A^2$ is a phenyl group or a pyridyl group, and hydrogens of the $A^1$ are both unsubstituted or substituted by a structure of Formula (i), Formula (ii) or Formula (iii), and at least one of hydrogens of the $A^2$ is substituted by the structure of Formula (i), Formula (ii) or Formula (iii):

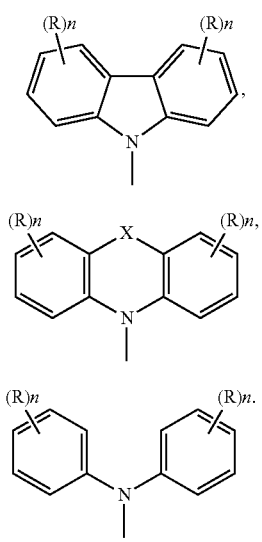

In Formula (i) to Formula (iii), n is independently an integer of 0 to 4, R is independently a monovalent group having 1 to 60 carbon atoms, X is —$NR^{14}$—, —S— or —$CR^{15}R^{16}$—, and $R^{14}$, $R^{15}$ and $R^{16}$ are independently —H, an alkyl group or an aryl group.

For the sake of conciseness, "the compound including the structure of Formula (I)" is also written as "the compound (I)" in the present disclosure.

With the combination of a main body of the pyridyl group of the $A^1$, the ketone group and a main body of the phenyl group/pyridyl group of the $A^2$ being electron accepting group, and the structure of Formula (i), Formula (ii) or Formula (iii) being electron donating group, the compound (I) is featured with TADF property. When the compound (I) is driven by a voltage, the compound (I) can release energy in the form of fluorescence and delayed fluorescence. Therefore, it is favorable to use the compound (I) as a dopant in an emitting layer of an OLED, which provides the OLED with advantages of high efficiency, low cost and capable of providing a wide light color tenability.

The aforementioned "main body of the pyridyl group" refers to the cyclic structure encircled by the carbon atoms and the nitrogen atom, but not including the hydrogen atoms or other substituents connecting with the carbon atoms. Similarly, the aforementioned "main body of the phenyl group" refers to the cyclic structure encircled by the carbon atoms, but not including the hydrogen atoms or other substituents connecting with the carbon atoms.

Specifically, R can be a straight-chain or branched aliphatic group having 1 to 60 carbon atoms, a cyclic aliphatic group having 1 to 60 carbon atoms, an aryl group having 1 to 60 carbon atoms or a heterocyclic group having 1 to 60 carbon atoms. Preferably, R is a group which can enhance the electron donating ability of the structure of Formula (i), Formula (ii) or Formula (iii). More specifically, R can be a methyl group, an ethyl group, a t-butyl group or a carbazole group.

The compound (I) can include a structure of Formula (I-1):

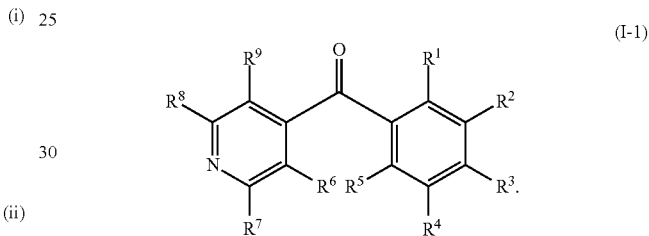
(I-1)

In Formula (I-1), $R^1$, $R^2$, $R^3$, $R^4$ and $R^5$ are independently —H, the structure of Formula (i), the structure of Formula (ii) or the structure of Formula (iii), at least one of the $R^1$, $R^2$, $R^3$, $R^4$ and $R^5$ is the structure of Formula (i), the structure of Formula (ii) or the structure of Formula (iii), and $R^6$, $R^7$, $R^8$ and $R^9$ can independently be an electron withdrawing group, an electron donating group or —H. The electron withdrawing group can be but is not limited to —CN or —F. The electron donating group can be but is not limited to the structure of Formula (i), the structure of Formula (ii) or the structure of Formula (iii). For example, the electron donating group can be a carbazole group or a diphenyl amine group.

Examples of the structure of Formula (I-1) can be but are not limited to structures of Formula (I-1-1) to Formula (I-1-7):

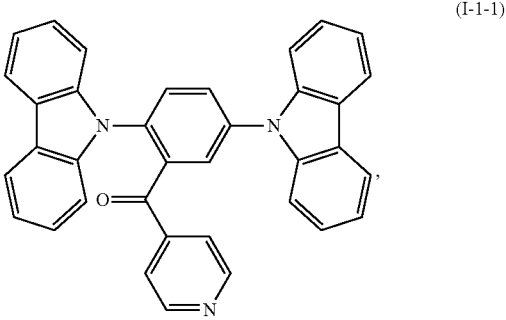
(I-1-1)

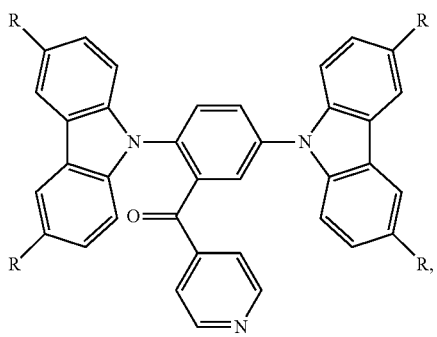

(I-1-2)

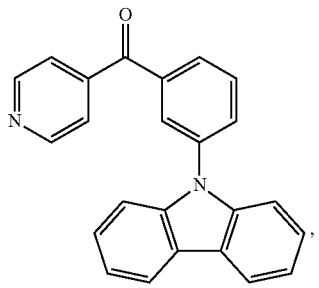

(I-1-6)

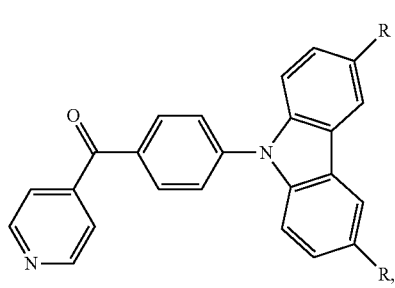

(I-1-3)

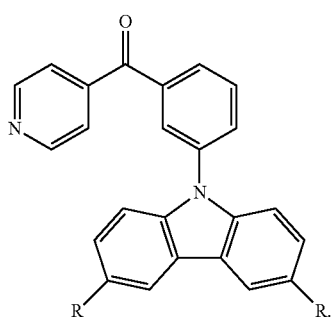

(I-1-7)

(I-1-4)

(I-1-5)

In Formula (I-1), when $R^2$, $R^3$ and $R^5$ are —H, $R^1$ and $R^4$ are the structure of Formula (i), n=0, and $R^6$, $R^7$, $R^8$ and $R^9$ are —H, the structure of Formula (I-1-1) can be obtained. In Formula (I-1), when $R^2$, $R^3$ and $R^5$ are —H, $R^1$ and $R^4$ are the structure of Formula (i), n=1, and $R^6$, $R^7$, $R^8$ and $R^9$ are —H, the structure of Formula (I-1-2) can be obtained. In Formula (I-1), when $R^1$, $R^2$, $R^4$ and $R^5$ are —H, $R^3$ is the structure of Formula (i), n=1, and $R^6$, $R^7$, $R^6$ and $R^9$ are —H, the structure of Formula (I-1-3) can be obtained. In Formula (I-1), when $R^1$, $R^3$ and $R^5$ are —H, $R^2$ and $R^4$ are the structure of Formula (i), n=0, and $R^6$, $R^7$, $R^8$ and $R^9$ are —H, the structure of Formula (I-1-4) can be obtained. In Formula (I-1), when $R^1$, $R^3$ and $R^5$ are —H, $R^2$ and $R^4$ are the structure of Formula (i), n=1, and $R^6$, $R^7$, $R^8$ and $R^9$ are —H, the structure of Formula (I-1-5) can be obtained. In Formula (I-1), when $R^1$, $R^2$, $R^3$ and $R^5$ are —H, $R^4$ is the structure of Formula (i), n=0, and $R^6$, $R^7$, $R^8$ and $R^9$ are —H, the structure of Formula (I-1-6) can be obtained. In Formula (I-1), when $R^1$, $R^2$, $R^3$ and $R^5$ are —H, $R^4$ is the structure of Formula (i), n=1, and $R^6$, $R^7$, $R^8$ and $R^9$ are —H, the structure of Formula (I-1-7) can be obtained.

The compound (I) can include a structure of Formula (I-2):

(I-2)

In Formula (I-2), $R^{21}$, $R^{22}$, $R^{23}$, $R^{24}$, $R^{25}$, $R^{26}$, $R^{27}$ and $R^{28}$ are independently —H, the structure of Formula (i), the structure of Formula (ii) or the structure of Formula (iii), and at least one of the $R^{21}$, $R^{22}$, $R^{23}$, $R^{24}$, $R^{25}$, $R^{26}$, $R^{27}$ and $R^{28}$ is the structure of Formula (i), the structure of Formula (ii) or the structure of Formula (iii).

An example of the structure of Formula (I-2) can be but is not limited to a structure of Formula (I-2-1):

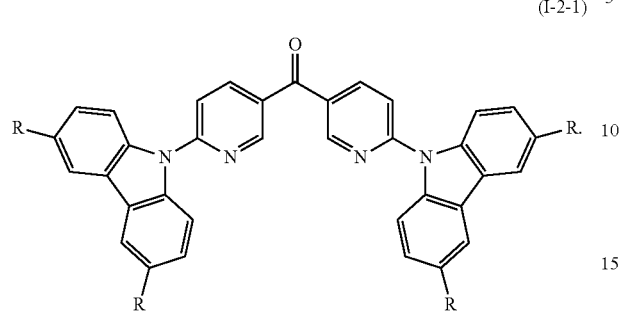

(I-2-1)

In Formula (I-2), when $R^{21}$, $R^{22}$, $R^{24}$, $R^{25}$, $R^{27}$ and $R^{28}$ are —H, $R^{23}$ and $R^{26}$ are the structure of Formula (i), and n=1, the structure of Formula (I-2-1) can be obtained.

The compound (I) can include a structure of Formula (I-3):

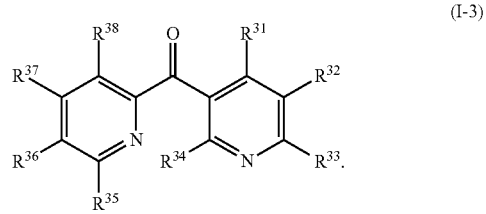

(I-3)

In Formula (I-3), $R^{31}$, $R^{32}$, $R^{33}$ and $R^{34}$ are independently —H, the structure of Formula (i), the structure of Formula (ii) or the structure of Formula (iii), at least one of the $R^{31}$, $R^{32}$, $R^{33}$ and $R^{34}$ is the structure of Formula (i), the structure of Formula (ii) or the structure of Formula (iii), and $R^{35}$, $R^{36}$, $R^{37}$ and $R^{38}$ are —H.

An example of the structure of Formula (I-3) can be but is not limited to a structure of Formula (I-3-1):

(I-3-1)

In Formula (I-3), when $R^{31}$, $R^{32}$ and $R^{34}$ are —H, $R^{33}$ is the structure of Formula (i), and n=1, the structure of Formula (I-3-1) can be obtained.

Further examples of the structures of Formula (I-1-1) to Formula (I-1-7), Formula (I-2-1) and Formula (I-3-1) can be but are not limited to the compounds listed in Table 1.

TABLE 1

| Formula | R | Abbreviation of compound name |
|---|---|---|
| (I-1-1) | | DCBPy |
| (I-1-2) | t-butyl group | DTCBPy |
| (I-1-3) | t-butyl group | pTCBPy |
| (I-1-3) | carbazole group | p3CzBPy |
| (I-1-4) | | mDCBPy |
| (I-1-5) | t-butyl group | mDTCBPy |
| (I-1-6) | | mCBPy |
| (I-1-7) | t-butyl group | mTCBPy |
| (I-1-7) | carbazole group | m3CzBPy |
| (I-2-1) | t-butyl group | 3BP-pDTC |
| (I-3-1) | t-butyl group | 3BP-pTC |
| (I-3-1) | carbazole group | 3BP-p3C |

Emitting Layer of OLED

FIG. 1 is a schematic cross-sectional view illustrating an emitting layer 140 of an OLED according to one embodiment of the present disclosure. In FIG. 1, the emitting layer 140 includes a host material 141 and a dopant 142, wherein the dopant 142 is the aforementioned compound (I). Thus, the OLED including the emitting layer 140 is featured with advantages of high efficiency, low cost and capable of providing a wide light color tenability. The details of the compound (I) have been recited previously and will not be repeated herein.

A doping concentration of the dopant 142 in the emitting layer 140 can be in a range of 5 wt % to 30 wt %.

By doping the dopant 142 in the emitting layer 140, the energy of the host material 141 can be transferred to the dopant 142, so that the light color and the luminous efficiency of the host material 141 can be changed, which can broaden the application of the OLED.

The host material 141 can be a high triplet energy host material, a hole transport type host material, an electron transport type host material or a bi-polar type host material. Specifically, the proper host material 141 can be decided according to actual demands. For example, the proper host material 141 can be decided according to the desired light color of the OLED. The host material 141 can include any one of structures of Formula (1) to Formula (9):

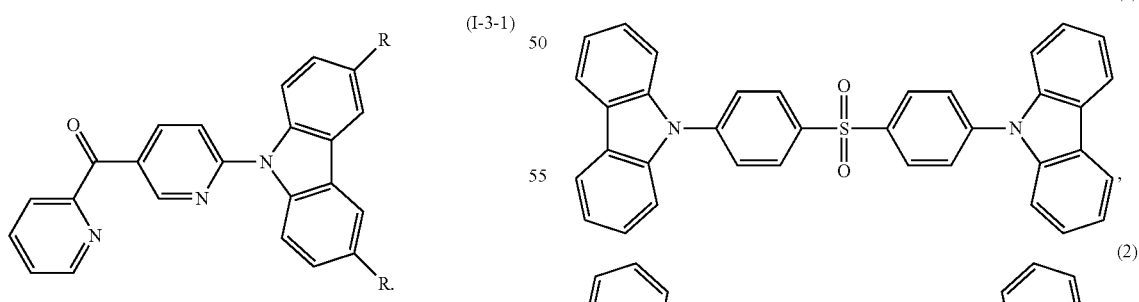

(3)
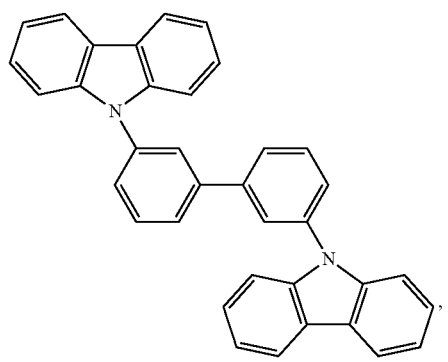

(4)
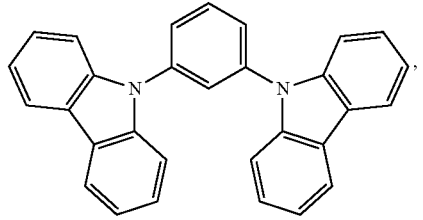

(5)
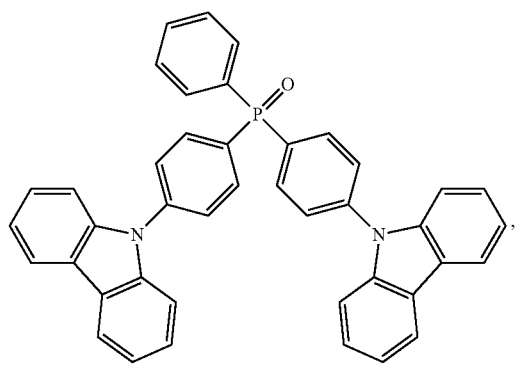

(6)
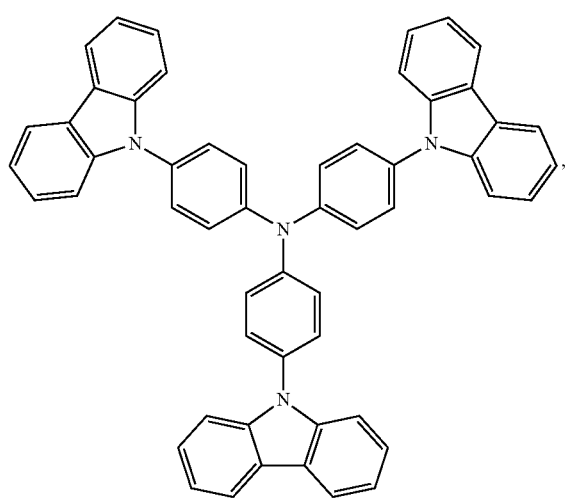

(7)
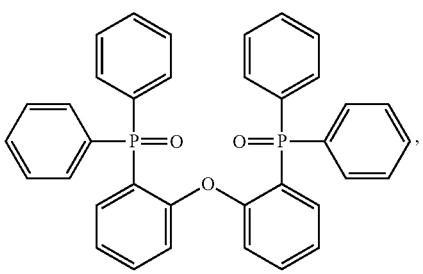

(8)
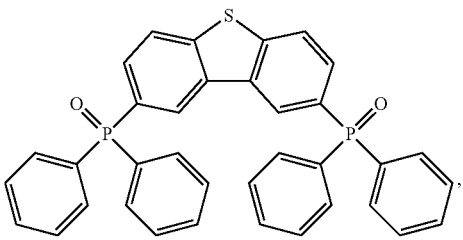

(9)
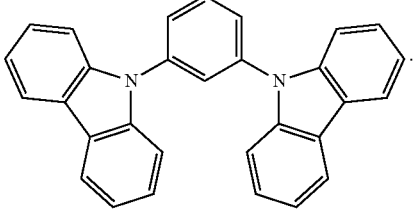

The compound name of Formula (1) is 9,9'-(sulfonylbis (4,1-phenylene))bis(9H-carbazole), and the abbreviation thereof is CzPS. The compound name of Formula (2) is 4,4'-di(9H-carbazol-9-yl)-1,1'-biphenyl, and the abbreviation thereof is CBP. The compound name of Formula (3) is 3,3'-di(9H-carbazol-9-yl)-1,1'-biphenyl, and the abbreviation thereof is mCBP. The compound name of Formula (4) is 1,3-di(9H-carbazol-9-yl)benzene, and the abbreviation thereof is mCP. The compound name of Formula (5) is bis(4-(9H-carbazol-9-yl)phenyl)(phenyl)phosphine oxide, and the abbreviation thereof is BCPO. The compound name of Formula (6) is tris(4-(9H-carbazol-9-yl)phenyl)amine, and the abbreviation thereof is TCTA. The compound name of Formula (7) is oxybis(2,1-phenylene))bis(diphenylphosphine oxide, and the abbreviation thereof is DPEPO. The compound name of Formula (8) is dibenzo[b,d]thiophene-2,8-diylbis(diphenylphosphine oxide, and the abbreviation thereof is PPT. The compound name of Formula (9) is 1,3,5-tri(9H-carbazol-9-yl)benzene, and the abbreviation thereof is TCB. The compounds of Formula (1) and (3)-(9) can be used to manufacture blue, green or red OLEDs. The compound of Formula (2) can be used to manufacture green or red OLEDs.

OLED Device

An OLED device includes the aforementioned emitting layer of the OLED. Thus, the OLED device including the emitting layer 140 is featured with advantages of high efficiency, low cost and capable of providing a wide light color tenability.

Figure 2:
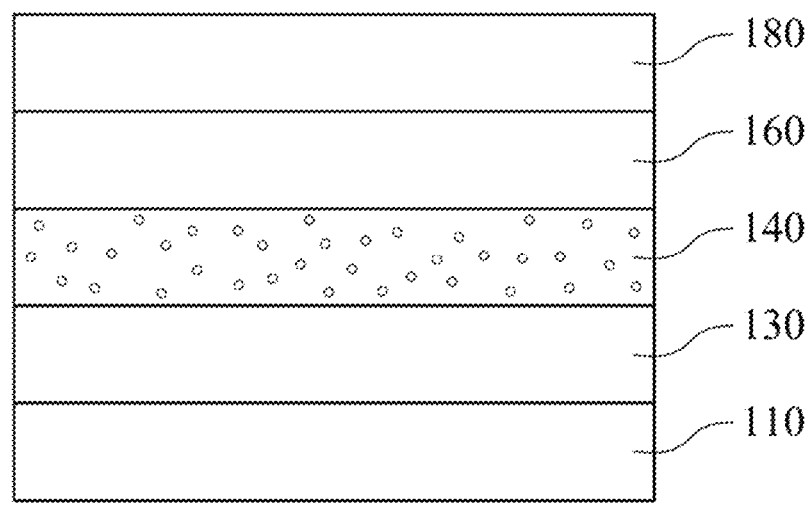
FIG. 2 is a schematic cross-sectional view illustrating an OLED device according to another embodiment of the present disclosure.

FIG. 2 is a schematic cross-sectional view illustrating an OLED device 100 according to another embodiment of the present disclosure. In FIG. 2, the OLED device 100 includes an anode 110, a hole-transporting layer 130, an emitting layer 140, an electron-transporting layer 160 and a cathode 180. The details of the emitting layer 140 have been recited previously and will not be repeated herein.

Specifically, the anode 110 can be a transparent conductive metal oxide or metal. The transparent conductive metal oxide can be ITO ($SnO_2:In_2O_3$), ZnO or AZO (Al:ZnO). The metal can be Ni, Au or Pt. When the anode 110 is the metal, a thickness of the anode 110 is preferably less than 15 nm.

A thickness of the hole-transporting layer 130 can be but is not limited to 200 Å to 600 Å.

A thickness of the electron-transporting layer 160 can be but is not limited to 300 Å to 700 Å.

The cathode 180 can be but is not limited to a mixture of Mg and Ag, a mixture of LiF and Al, or Al.

The OLED device 100 can further include a substrate (not shown). The LED device 100 can be manufactured by sequentially depositing the anode 110, the hole-transporting layer 130, the emitting layer 140, the electron-transporting layer 160 and the cathode 180 on the substrate. The substrate can be a transparent glass substrate or a plastic substrate.

Figure 3:
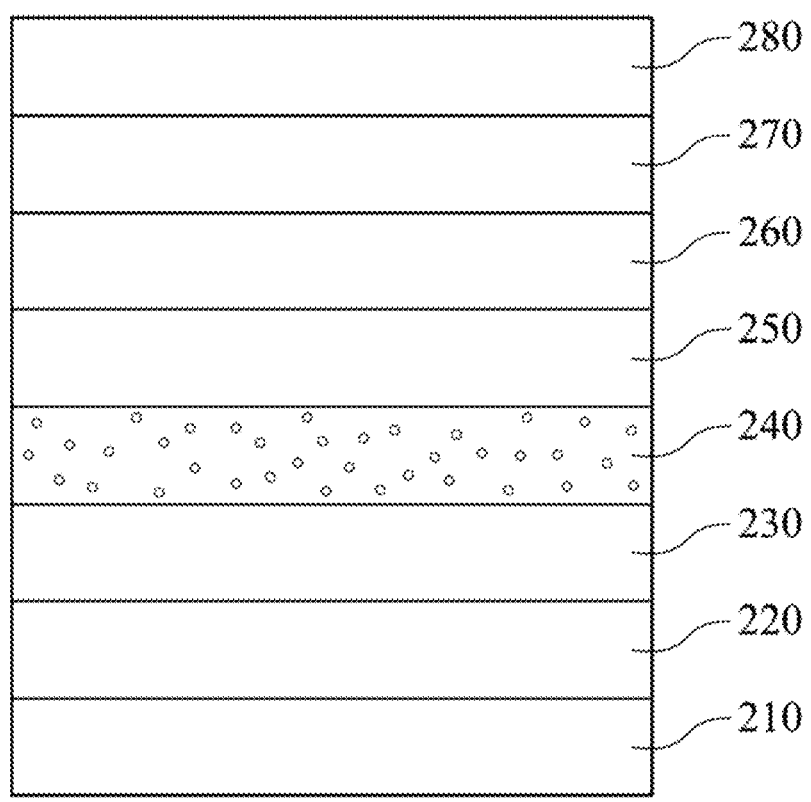
FIG. 3 is a schematic cross-sectional view illustrating an OLED device according to yet another embodiment of the present disclosure.

FIG. 3 is a schematic cross-sectional view illustrating an OLED device 200 according to yet another embodiment of the present disclosure. In FIG. 3, the OLED device 200 includes an anode 210, a hole injection layer 220, a hole-transporting layer 230, an emitting layer 240, an exciton blocker 250, an electron-transporting layer 260, an electron injection layer 270, and a cathode 280.

The hole injection layer 220 is a material with a HOMO energy level which can increase the transport of holes between the anode 210 and the hole-transporting layer 230. A thickness of the hole injection layer 220 can be but is not limited to 200 Å to 500 Å.

A thickness of the exciton blocker 250 can be but is not limited to 50 Å to 200 Å.

A thickness of the electron injection layer 270 can be but is not limited to 7 Å to 15 Å.

The other details of the OLED device 200 can be the same as that of the OLED device 100 in FIG. 2, and will not be repeated herein.

Synthesis of Examples and Comparative Examples

Ex. 1: DCBPy

The structure of DCBPy can refer to Formula (I-1-1). DCBPy can be synthesized according to Scheme 1:

Scheme 1.

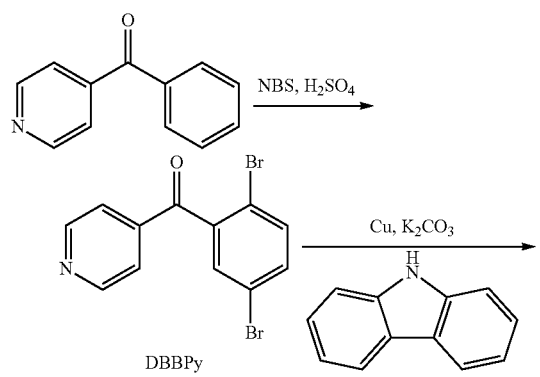

-continued

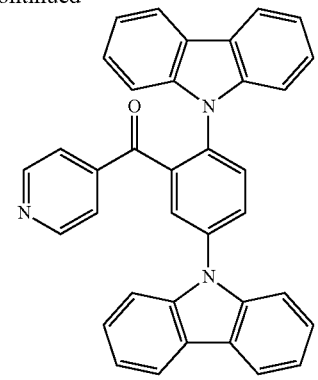

In Scheme 1, DCBPy is synthesized by two steps, the first step and the second step.

In the first step, (2,5-dibromophenyl)(pyridine-4-yl)methanone (DBBPy) is synthesized as follows. To a stirred solution of 4-benzoylpyridine (6.00 g, 32.8 mmol) in conc. $H_2SO_4$ (20 mL) at 60° C., N-bromosuccinimide (NBS) (14.0 g, 78.7 mmol) was added in four portions with 5 min interval. Then, the reaction was continued for 4 hours at the same temperature and the solution was poured into crushed ice slowly, followed by basification with $Na_2CO_3$. The solution was extracted with EtOAc twice (2×100 ml) and the combined organic layer was washed with water. The solvent was evaporated under reduced pressure and then purified by a silica gel column (hexane/ethyl acetate (1:5)) to afford the compound DBBPy with 82% yield. From the results of $^1$H NMR and High-resolution mass spectrometer (HRMS), it can confirm that the product of the first step is DBBPy. $^1$H NMR (400 MHz, $CDCl_3$): δ 8.83-8.80 (m, 2H), 7.57-7.55 (m, 2H), 7.51-7.50 (m, 2H), 7.47 (d, J=1.4 Hz, 1H). HRMS (EI, m/z): [M$^+$] cal for $C_{12}H_7Br_2NO$ 338.8894, found 338.8891.

In the second step, DCBPy is synthesized as follows. To an oven-dried seal tube DBBPy (2.50 g, 7.33 mmol), carbazole (3.06 g, 18.3 mmol), Cu (0.93 g, 14.7 mmol), $K_2CO_3$ (5.06 g, 36.7 mmol) and 1,2-dichlorobenzene (20 ml) was added. The system was evacuated and purged with nitrogen three times and the mixture was heated and stirred at 180° C. for 48 hours. The reaction mixture was filtered through Celite and washed with ethyl acetate (30 ml). Solvent was evaporated under reduced pressure and then purified by column chromatography (hexane/ethyl acetate (4:1)) to afford the desired yellow solid in 57% yield. The melting point (m.p.) of the product is 130° C. From the results of $^1$H NMR, $^{13}$C NMR and HRMS, it can confirm that the product of the second step is DCBPy. $^1$H NMR (400 MHz, $CDCl_3$): δ 8.21 (sd, J=2.4 Hz, 1H), 8.19 (d, J=7.6 Hz, 2H), 8.09 (dd, J=8.4 Hz, J=1.6 Hz, 1H), 7.92-7.90 (m, 3H), 7.83 (d, J=7.6 Hz, 2H), 7.65 (d, J=8.4 Hz, 2H), 7.53-7.49 (m, 2H), 7.45-7.41 (m, 2H), 7.38 (m, 4H), 7.23 (t, J=7.6 Hz, 2H), 6.68 (dd, J=8.4 Hz, J=1.6 Hz, 2H); $^{13}$C NMR (100 MHz, $CDCl_3$): δ 194.96 (CO), 148.78 (2CH), 142.07 (C), 140.51 (2C), 140.21 (2C), 138.07 (C), 137.21 (C), 134.82 (C), 131.47 (CH), 130.46 (CH), 129.31 (CH), 126.35 (2CH), 126.16 (2CH), 123.84 (2C), 123.19 (2C), 120.81 (2CH), 120.77 (2CH), 120.60 (2CH), 120.38 (2 CH), 119.90 (2CH), 109.53 (4 CH); HRMS (EI, m/z): [M$^+$] cal for $C_{36}H_{23}N_3O$ 513.1841, found 513.1837.

Ex. 2: DTCBPy

The structure of DTCBPy can refer to Formula (I-1-2), wherein R is a t-butyl group. The synthesis of DTCBPy is similar to that of Ex. 1, but replace the carbazole (3.06 g, 18.3 mmol) in the second step with 3,6-di-t-butyl-9H-carbazole (5.11 g, 18.3 mmol), so that a yellow solid in 61% yield can be obtained. The m.p. of the product is 306° C. From the results of $^1$H NMR, $^{13}$C NMR and HRMS, it can confirm that the product is DTCBPy. $^1$H NMR (400 MHz, CDCl$_3$): δ 8.17 (s, 3H), 8.06 (dd, J=8.4 Hz, J=2.4 Hz, 1H), 7.88 (s, 1H), 7.87-7.85 (m, 2H), 7.81-7.80 (m, 2H), 7.59-7.53 (m, 4H), 7.47 (dd, J=8.8 Hz, J=2.0 Hz, 2H), 7.25 (d, J=8.8 Hz, 2H), 6.65-6.63 (m, 2H), 1.49 (s, 18H), 1.44 (s, 18H); $^{13}$C NMR (100 MHz, CDCl$_3$): δ 194.95 (CO), 148.63 (2CH), 143.84 (2C), 143.79 (2C), 142.03 (C), 139.22 (2C), 138.67 (2C), 138.23 (C), 136.59 (C), 135.01 (C), 130.95 (CH), 130.13 (CH), 128.97 (CH), 123.98 (2CH), 123.89 (2C), 123.76 (2CH), 123.38 (2C), 119.92 (2CH), 116.53 (2CH), 116.36 (2CH), 109.07 (4 CH), 34.79 (2C), 34.73 (2C), 31.97 (6 CH$_3$), 31.95 (6 CH$_3$). HRMS (El, m/z): [M$^+$] cal for C$_{52}$H$_{55}$N$_3$O 737.4345, found 737.4338.

Ex. 3: mDCBPy

The structure of mDCBPy can refer to Formula (I-1-4). mDCBPy can be synthesized according to Scheme 2:

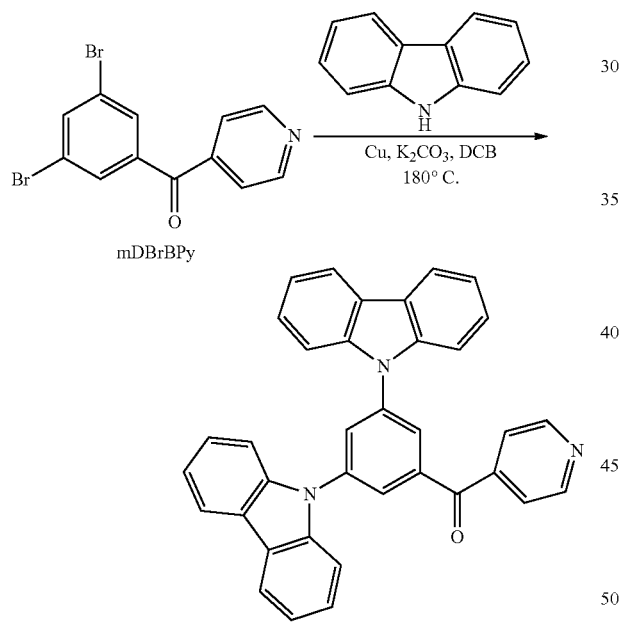

mDCBPy can be synthesized as follows. To a dried seal tube (3,5-dibromophenyl)(pyridin-4-yl)methanone (mDBrBPy) (2.5 g, 7.33 mmol), carbazole (3.06 g, 18.3 mmol), Cu (0.93 g, 14.7 mmol), K$_2$CO$_3$ (5.06 g, 36.7 mmol) and 1,2-dichlorobenzene (20 ml) were added. The reaction tube was evacuated and purged with nitrogen gas three times under stirring followed by heating at 180° C. for 48 hours. The reaction mixture was filtered through Celite and washed with ethyl acetate (30 ml). The solvent was evaporated under reduced pressure followed by column chromatography purification using EtOAc/n-hexane (1:3) as eluent afforded yellow solid in 57% yield. The m.p. of the product is 219° C. From the results of $^1$H NMR, $^{13}$C NMR and HRMS, it can confirm that the product is mDCBPy $^1$H NMR (400 MHz, CDCl$_3$): δ 8.85-8.83 (m, 2H), 8.14 (d, J=8.0 Hz, 4H), 8.13-8.11 (m, 3H), 7.72-7.71 (m, 2H), 7.54 (d, J=8.0 Hz, 4H), 7.47-7.43 (m, 4H), 7.35-7.31 (m, 4H); $^{13}$C NMR (100 MHz, CDCl$_3$): δ 193.47 (—CO—), 150.67, 143.23, 140.13, 140.05, 139.24, 129.49, 126.51, 126.39, 123.81, 122.66, 120.87, 120.64, 109.29; HRMS (FAB$^+$) cal for C$_{36}$H$_{23}$N$_3$O 513.1841, found 513.1840.

Ex. 4: mDTCBPy

The structure of mDTCBPy can refer to Formula (I-1-5), wherein R is a t-butyl group. mDTCBPy can be synthesized according to Scheme 3:

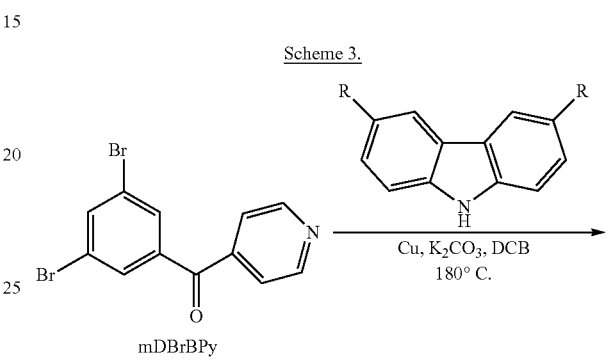

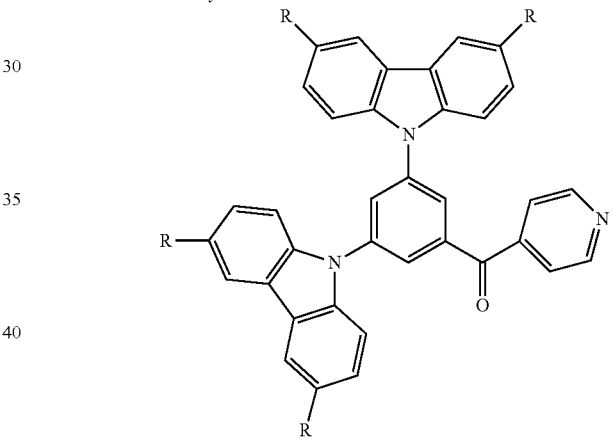

mDTCBPy can be synthesized as follows. To an oven dried seal tube mDBrBPy (2.50 g, 7.33 mmol), t-butyl carbazole (5.11 g, 18.3 mmol), Cu (0.93 g, 14.7 mmol), K$_2$CO$_3$ (5.06 g, 36.7 mmol) and 1,2-dichlorobenzene (20 ml) was added. The system was evacuated and nitrogen was purged and the mixture was stirred at 180° C. for 48 hours. After completion of reaction, reaction mixture was filtered through Celite and washed with 50 ml of ethyl acetate. Solvent was evaporated under reduced pressure followed by column chromatography purification using n-hexane/EtOAc (3:1) as eluent afforded yellow solid in 78% yield. The m.p. of the product is 355° C. From the results of $^1$H NMR, $^{13}$C NMR and HRMS, it can confirm that the product is mDTCBPy. $^1$H NMR (400 MHz, CDCl$_3$): δ 8.84 (d, J=5.2 Hz, 2H), 8.13 (s, 4H), 8.09 (sd, J=1.6 Hz, 1H), 8.04 (sd, J=2.0 Hz, 2H), 7.71 (d, J=5.6 Hz, 2H), 7.49-7.44 (m, 8H), 1.44 (s, 36H); $^{13}$C NMR (100 MHz, CDCl$_3$): δ 194.35 (—CO—), 150.48, 143.85, 143.44, 138.84, 138.75, 137.65, 131.46, 130.22, 128.32, 127.76, 123.80, 123.60, 122.82, 116.43, 108.79, 34.72, 31.94; HRMS (FAB$^+$) cal for C$_{52}$H$_{55}$N$_3$O 737.4345, found 737.4335.

Ex. 5: mTCBPy

The structure of mTCBPy can refer to Formula (I-1-7), wherein R is a t-butyl group. mTCBPy can be synthesized according to Scheme 4:

Scheme 4.

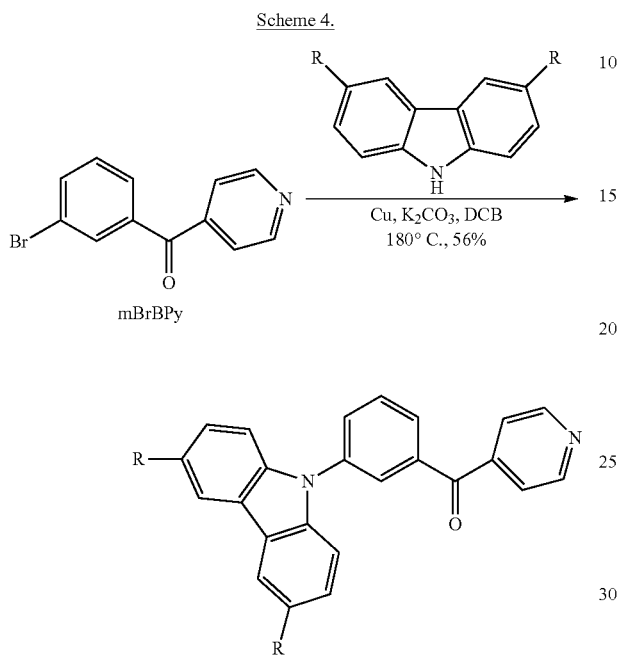

mBrBPy mTCBPy can be synthesized as follows. To an oven dried seal tube mBrBPy (2.5 g, 9.54 mmol), t-butyl carbazole (3.19 g, 11.40 mmol), Cu (0.61 g, 9.54 mmol), K$_2$CO$_3$ (3.29 g, 23.80 mmol) and 1,2-dichlorobenzene (20 ml) was added. The system was evacuated and nitrogen was purged and the mixture was stirred at 180° C. for 48 hours. After completion of reaction, reaction mixture was filtered through Celite and washed with 50 ml of ethyl acetate. Solvent was evaporated under reduced pressure followed by column chromatography purification using n-hexane/EtOAc (3:1) as eluent afforded yellow solid in 75% yield. The m.p. of the product is 194° C. From the results of $^1$H NMR, $^{13}$C NMR and HRMS, it can confirm that the product is mTCBPy. $^1$H NMR (400 MHz, CDCl$_3$): δ 8.82-8.81 (m, 2H), 8.14 (sd, J=1.6 Hz, 2H), 8.01 (st, J=1.6 Hz, 1H), 7.87-7.84 (m, 2H), 7.73 (d, J=7.8 Hz, 1H), 7.65-7.63 (m, 2H), 7.47 (dd, J=8.8 Hz, J=2.0 Hz, 2H), 7.35 (d, J=8.4 Hz, 2H), 1.46 (s, 18H); $^{13}$C NMR (100 MHz, CDCl$_3$): δ 194.38, 150.50, 143.83, 143.43, 138.82, 138.73, 137.64, 131.46, 130.23, 128.33, 127.75, 123.80, 123.59, 122.79, 116.43, 108.78, 34.73, 31.94; HRMS (FAB$^+$) cal for C$_{32}$H$_{32}$N$_2$O 460.2515, found 460.2518.

Ex. 6: 3BP-pTC

The structure of 3BP-pTC can refer to Formula (I-3-1), wherein R is a t-butyl group. 3BP-pTC can be synthesized according to Scheme 5:

Scheme 5.

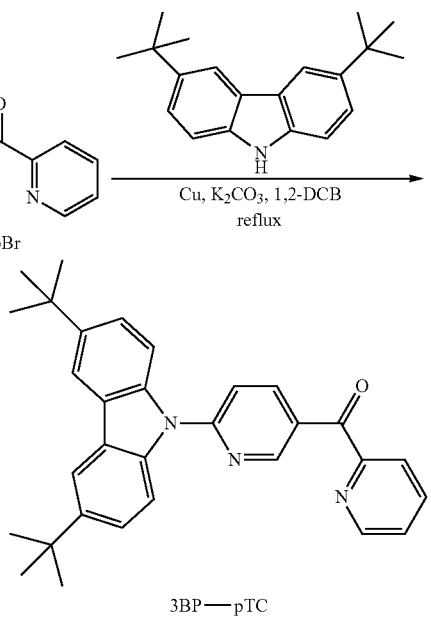

3BP—pBr

3BP—pTC

3BP-pTC can be synthesized as follows. To an oven dried seal tube was added (6-bromopyridin-3-yl)(pyridin-2-yl) methanone (3BP-pBr) (2.5 g. 9.5 mmol), t-butylcarbazole (3.18 g, 11.40 mmol), Cu (0.60 g, 9.5 mmol), K$_2$CO$_3$ (1.31 g, 19.00 mmol) and p-xylene (20 ml). It was evacuated and purged with nitrogen three times under stirring followed by heating at 150° C. for 12 hours. The reaction mixture was filtered through Celite and washed with ethyl acetate (30 ml). Evaporation of solvent under reduced pressure followed by column chromatography purification using n-hexane/ EtOAc (3:1) as eluent afforded yellow solid in 82% yield. The m.p. of the product is 217° C. From the results of $^1$H NMR, $^{13}$C NMR and HRMS, it can confirm that the product is 3BP-pTC. $^1$H NMR (400 MHz, CDCl$_3$): δ 9.48 (sd, J=2.0 Hz, 1H), 8.76 (d, J=4.4 Hz, 1H), 8.67 (dd, J=8.4 Hz, J=2.0 Hz, 1H), 8.17 (d, J=7.6 Hz, 1H), 8.08 (sd, J=1.6 Hz, 2H), 7.98 (d, J=8.8 Hz, 2H), 7.95-7.93 (m, 1H), 7.77 (d, J=8.4 Hz, 1H), 7.55-7.51 (m, 3H), 1.46 (s, 18H); $^{13}$C NMR (100 MHz, CDCl$_3$): δ 190.83 (—CO—), 154.40, 152.99, 152.98, 148.55, 144.82, 140.71, 137.42, 137.38, 128.08, 126.77, 125.07, 124.65, 124.15, 116.27, 116.14, 111.70, 34.76, 31.85; HRMS (FAB$^+$) cal for C$_{31}$H$_{31}$NO$_3$ 461.2467, found 461.2462.

Ex. 7: 3BP-pDTC

The structure of 3BP-pDTC can refer to Formula (I-2-1), wherein R is a t-butyl group. 3BP-pDTC can be synthesized according to Scheme 6:

Scheme 6.

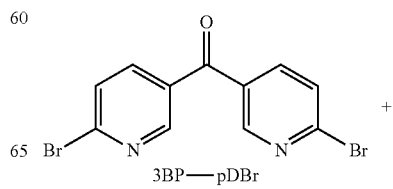

3BP—pDBr

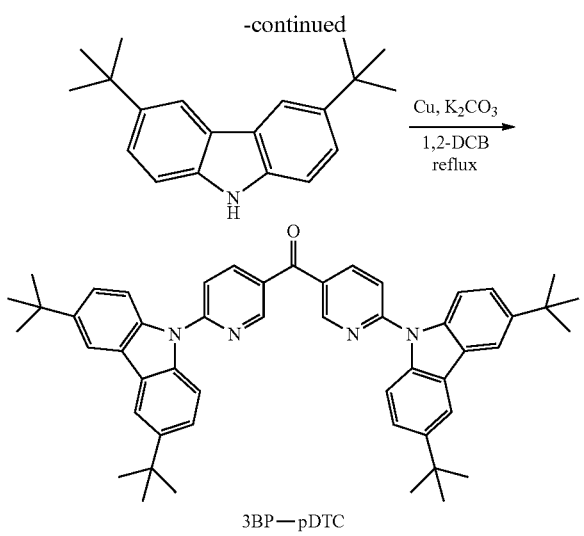

3BP—pDTC

3BP-pDTC can be synthesized as follows. To an oven dried seal tube was added bis(6-bromopyridin-3-yl)methanone (3BP-pDBr) (2.0 g, 5.85 mmol), t-butylcarbazole (3.59 g, 11.70 mmol), Cu (0.74 g, 11.69 mmol), $K_2CO_3$ (3.23 g, 23.40 mmol) and p-xylene (20 ml). It was evacuated and purged with nitrogen three times under stirring followed by heating at 150° C. for 12 hours. The reaction mixture was filtered through Celite and washed with 30 ml of ethyl acetate. Evaporation of solvent under reduced pressure followed by column chromatography purification using n-hexane/EtOAc (3:1) as eluent afforded yellow solid in 84% yield. The m.p. of the product is 400° C. From the results of $^1$H NMR, $^{13}$C NMR and HRMS, it can confirm that the product is 3BP-pDTC. $^1$H NMR (400 MHz, CDCl$_3$): δ 9.18 (sd, J=2.0 Hz, 2H), 8.42 (dd, J=8.4 Hz, J=2.4 Hz, 2H), 8.10 (sd, J=1.6 Hz, 4H), 8.01 (d, J=8.4 Hz, 4H), 7.85 (d, J=8.4 Hz, 2H), 7.53 (dd, J=8.8 Hz, J=2.0 Hz, 4H), 1.47 (s, 36H); $^{13}$C NMR (100 MHz, CDCl$_3$): δ 191.04 (—CO—), 155.37, 151.34, 145.15, 139.53, 137.34, 128.67, 125.25, 124.26, 116.67, 116.27, 111.73, 34.80, 31.85; HRMS (FAB$^+$) cal for $C_{51}H_{54}N_4O$ 738.4298, found 738.4293.

Comparative Ex. 1: DCPKPy

DCPKPy has a structure of Formula (II):

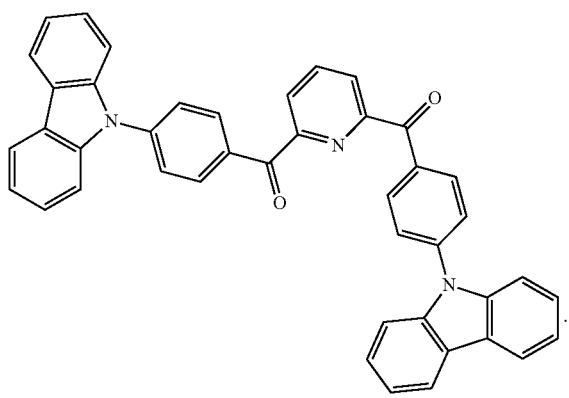

(II)

DCPKPy can be synthesized according to Scheme 7:

Scheme 7.

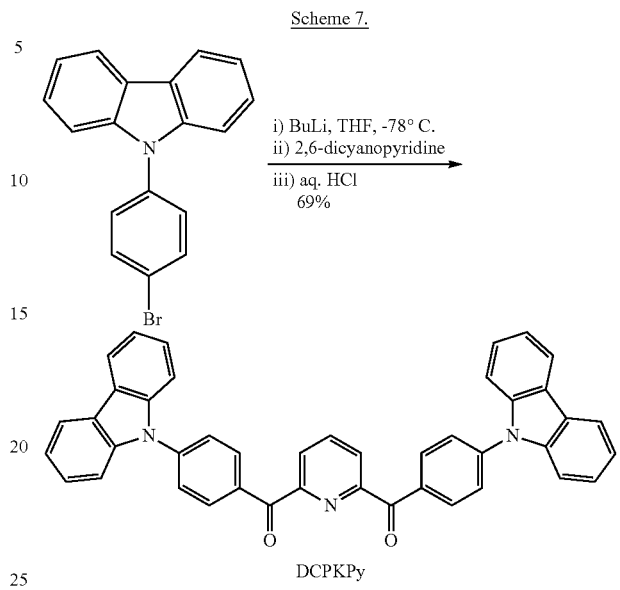

DCPKPy

DCPKPy can be synthesized as follows. To a stirred solution of 9-(4-bromophenyl)-9H-carbazole (2.87 g, 89.14 mmol) in THF (50 ml) at −78° C. was added n-BuLi (3.41 ml, 8.43 mmol) and stirred for 1 hour at the same temperature. To this solution, 1,3-dicyanopyridine (0.5 g, 3.87 mmol) in THF (20 ml) was added dropwise and the reaction mixture was allowed to stir for another 2 hours at −78° C. It was quenched with aq. HCl at 0° C. and partitioned between water and ethyl acetate. The organic layer was washed with water and dried with Na$_2$SO$_4$. Evaporation of solvent under reduced pressure followed by column chromatography purification afforded yellow solid in 69% yield. From the results of $^1$H NMR, $^{13}$C NMR and HRMS, it can confirm that the product is DCPKPy. $^1$H NMR (400 MHz, CDCl$_3$): δ 8.48 (d, J=8.0 Hz, 4H), 8.38 (d, J=7.6 Hz, 2H), 8.19 (t, J=7.6 Hz, 1H), 8.07 (d, J=7.6 Hz, 4H), 7.68 (d, J=8.4 Hz, 4H), 7.40 (d, J=8.0 Hz, 4H), 7.20 (t, J=7.8 Hz, 4H), 7.12 (t, J=7.8 Hz, 4H); $^{13}$C NMR (100 MHz, CDCl$_3$): δ 191.10 (—CO—), 153.78, 142.31, 139.97, 138.62, 134.08, 133.04, 127.27, 126.14, 125.87, 123.79, 120.58, 120.34, 109.57.

<Property Measurements of Examples and Comparative Examples>

Figure 4:
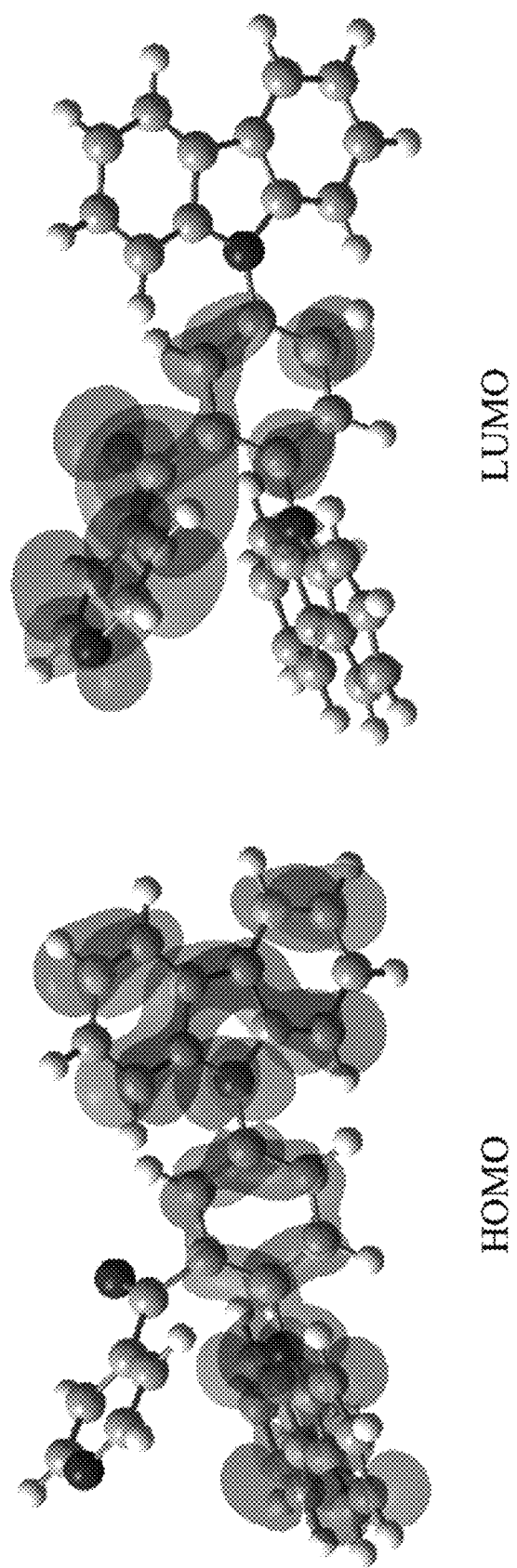
FIG. 4 shows molecular orbitals of Example 1 (Ex. 1)
Figure 5:
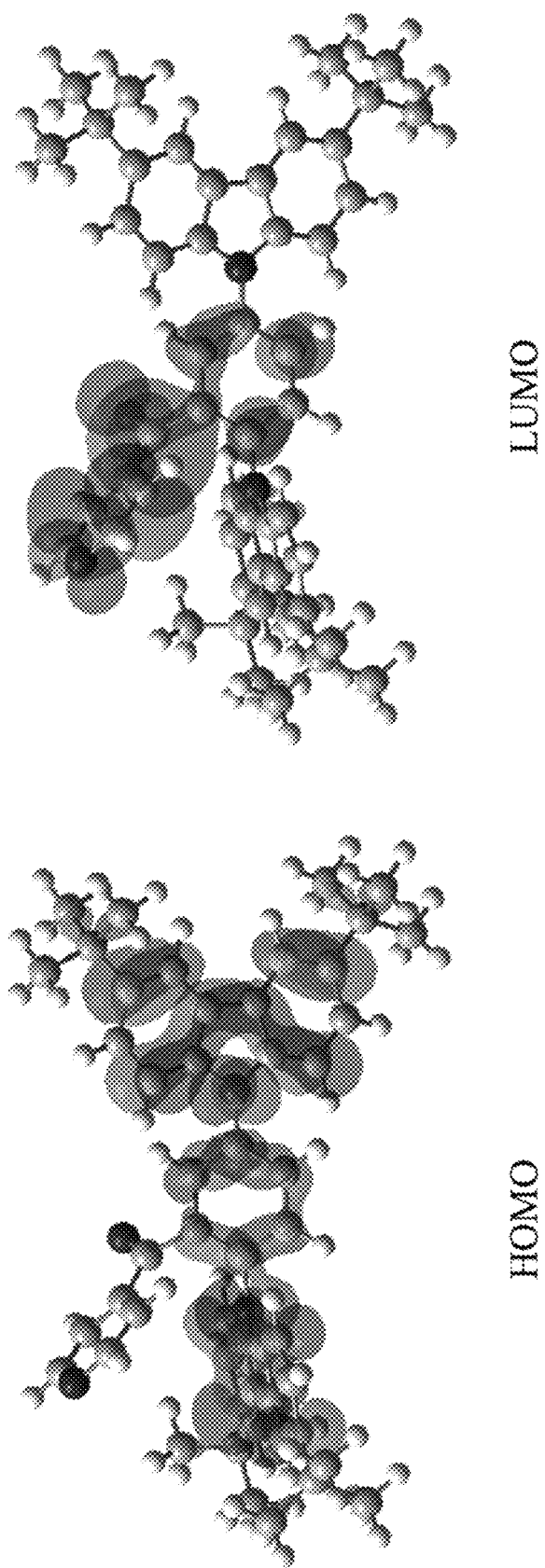
FIG. 5 shows molecular orbitals of Example 2 (Ex. 2)
Figure 6:
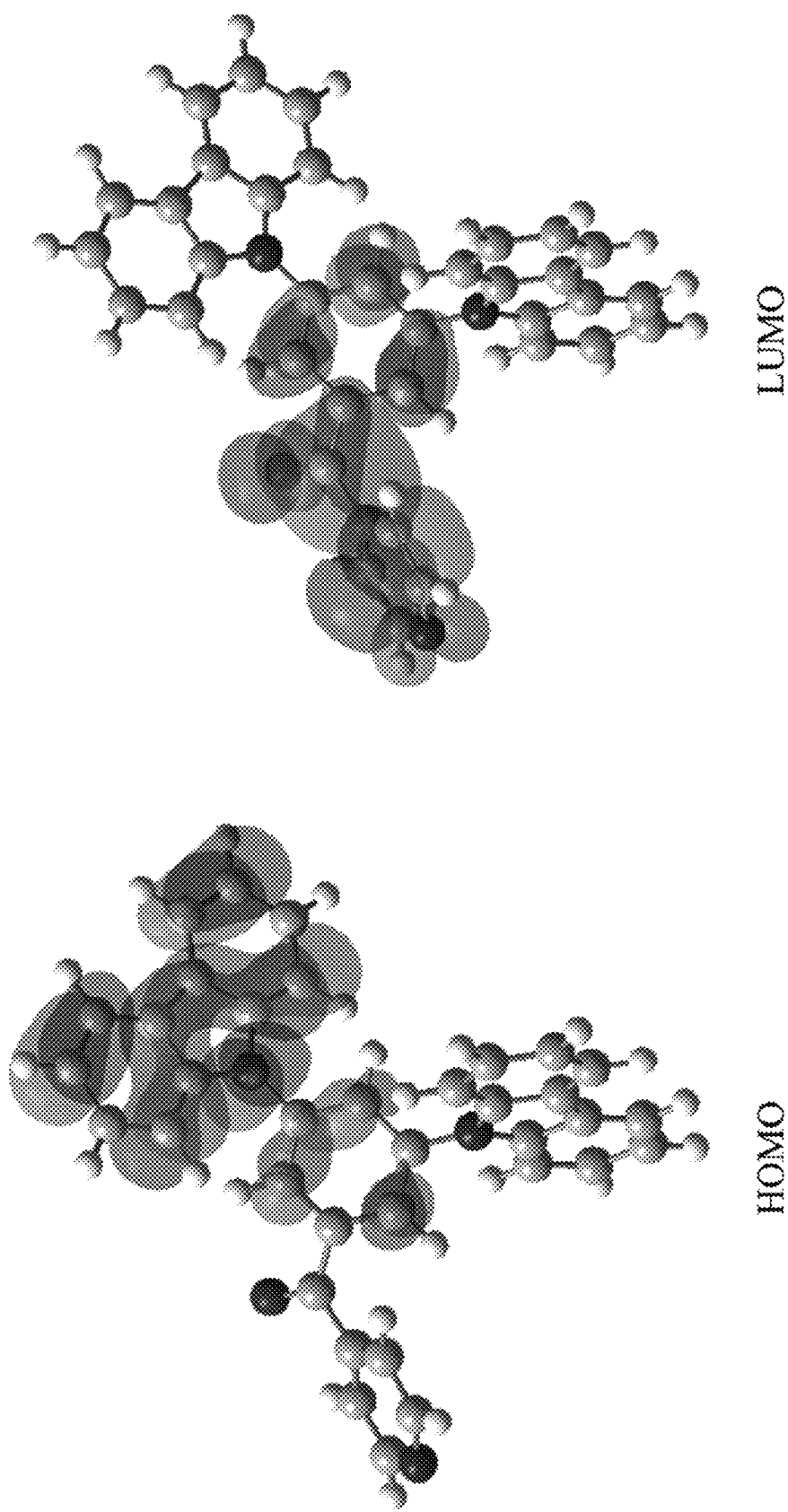
FIG. 6 shows molecular orbitals of Example 3 (Ex. 3)
Figure 7:
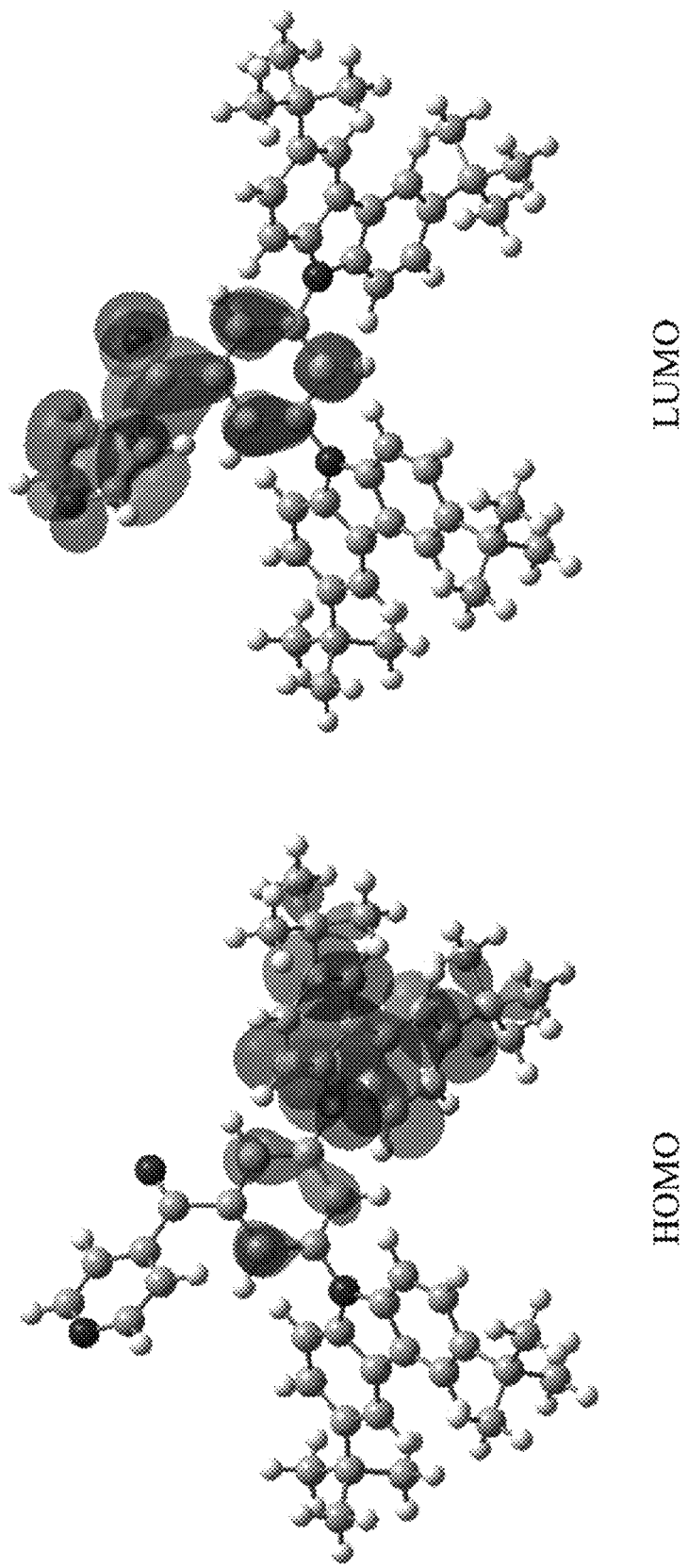
FIG. 7 shows molecular orbitals of Example 4 (Ex. 4)
Figure 8:
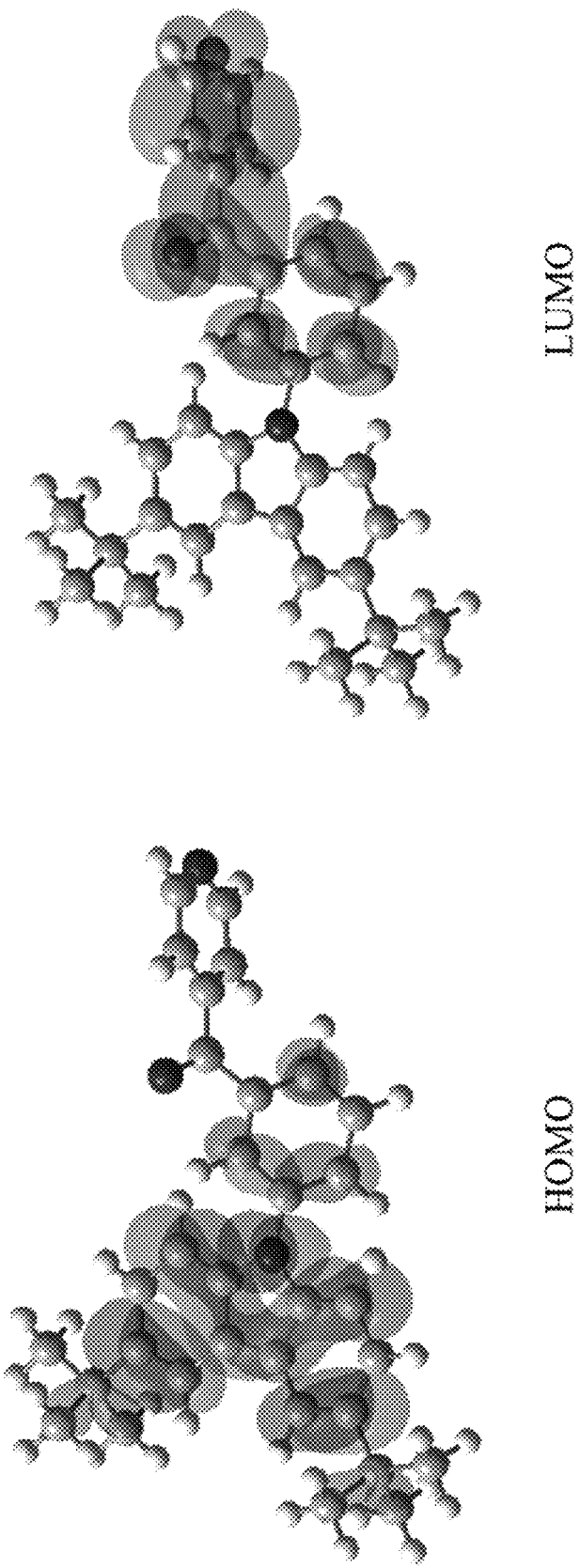
FIG. 8 shows molecular orbitals of Example 5 (Ex. 5)
Figure 9:
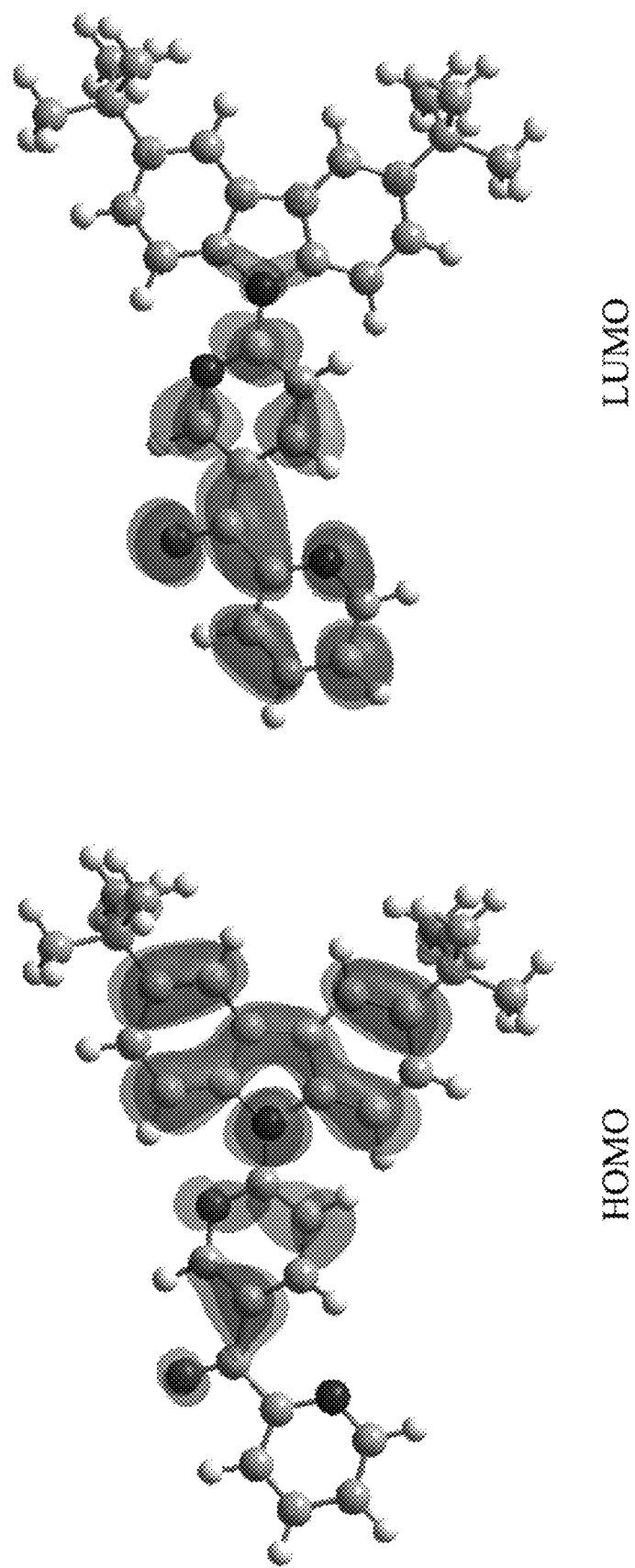
FIG. 9 shows molecular orbitals of Example 6 (Ex. 6)
Figure 10:
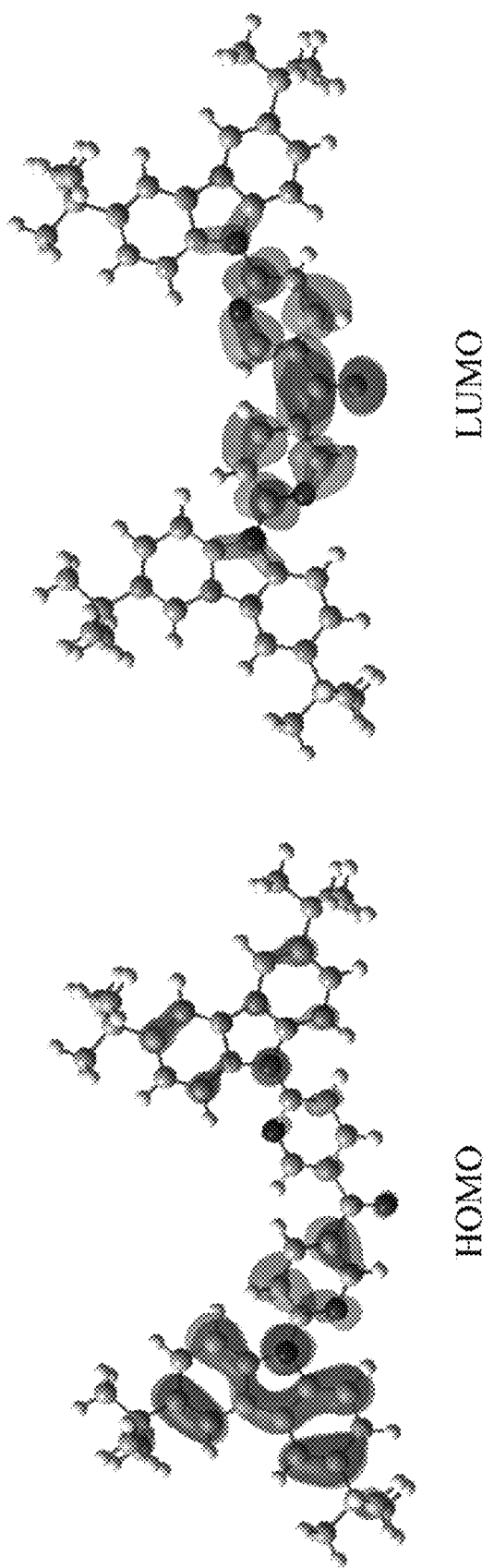
FIG. 10 shows molecular orbitals of Example 7 (Ex. 7)

FIG. 4 shows molecular orbitals of Ex. 1. FIG. 5 shows molecular orbitals of Ex. 2. FIG. 6 shows molecular orbitals of Ex. 3. FIG. 7 shows molecular orbitals of Ex. 4. FIG. 8 shows molecular orbitals of Ex. 5. FIG. 9 shows molecular orbitals of Ex. 6. FIG. 10 shows molecular orbitals of Ex. 7. FIG. 4 to FIG. 10 are obtained from the calculation results of time dependent density functional theory, and show the distribution of HOMOs and LUMOs of Ex. 1 to Ex. 7, respectively. As shown in FIG. 4 to FIG. 10, the HOMOs are mainly distributed over the electron donating group of carbazole group/3,6-di-t-butyl-carbazole group, the LUMOs are mainly distributed over the electron accepting group composed of the main body of the pyridyl group, the ketone group and the main body of the phenyl group/pyridyl group, and there is a small overlap between the HOMOs and the LUMOs, all of which show that Ex. 1 to Ex. 7 have TADF property.

Figure 11:
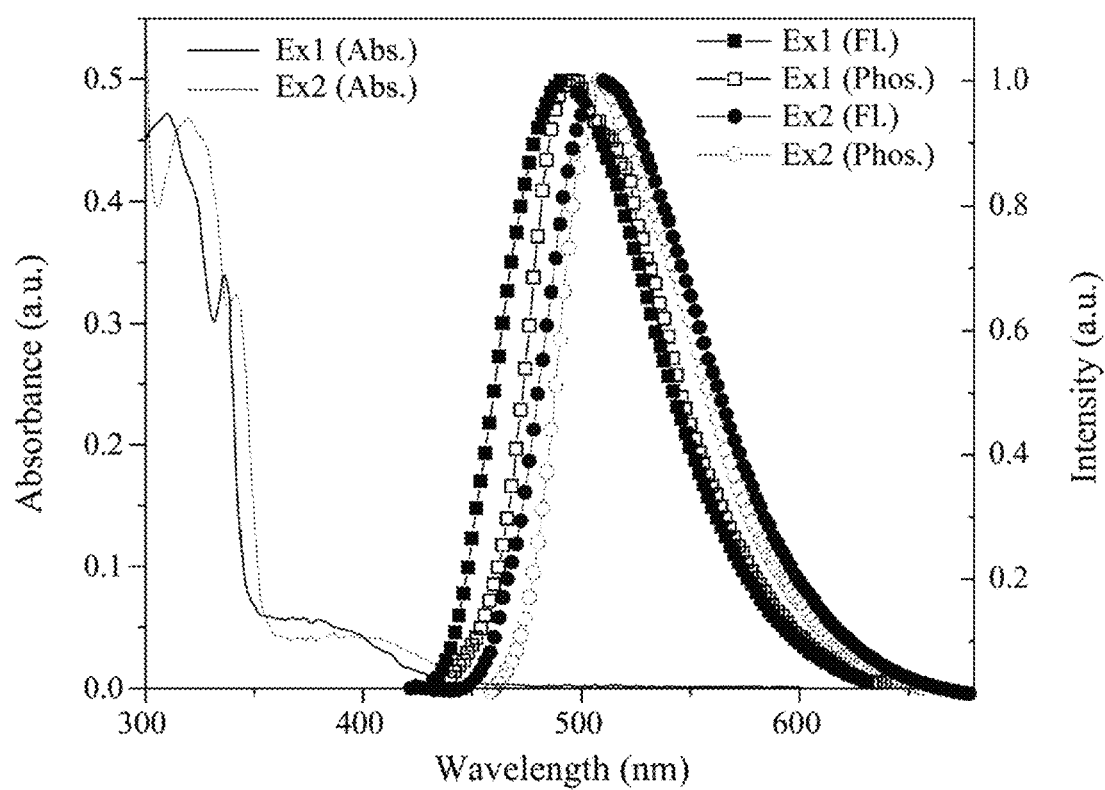
FIG. 11 shows absorption (Abs.) spectra, fluorescence (Fl.) spectra and phosphorescence (Phos.) spectra of Ex. 1 and Ex. 2.
Figure 12:
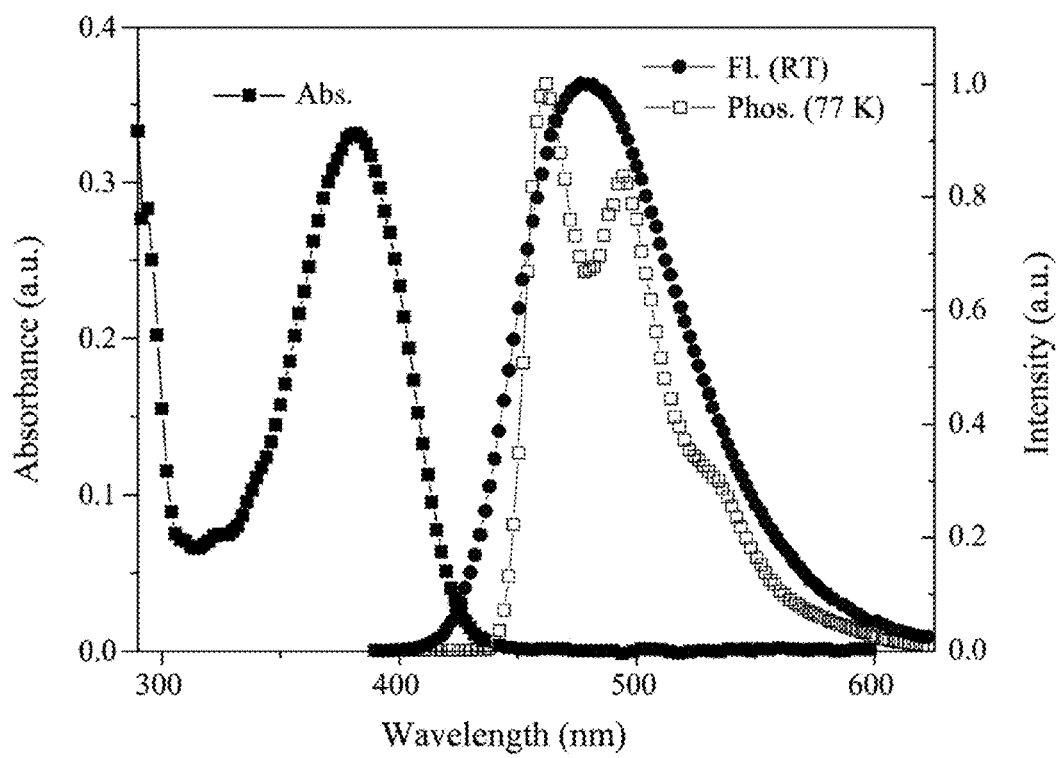
FIG. 12 shows an Abs. spectrum, a Fl. spectrum and a Phos. spectrum of Ex. 6.
Figure 13:
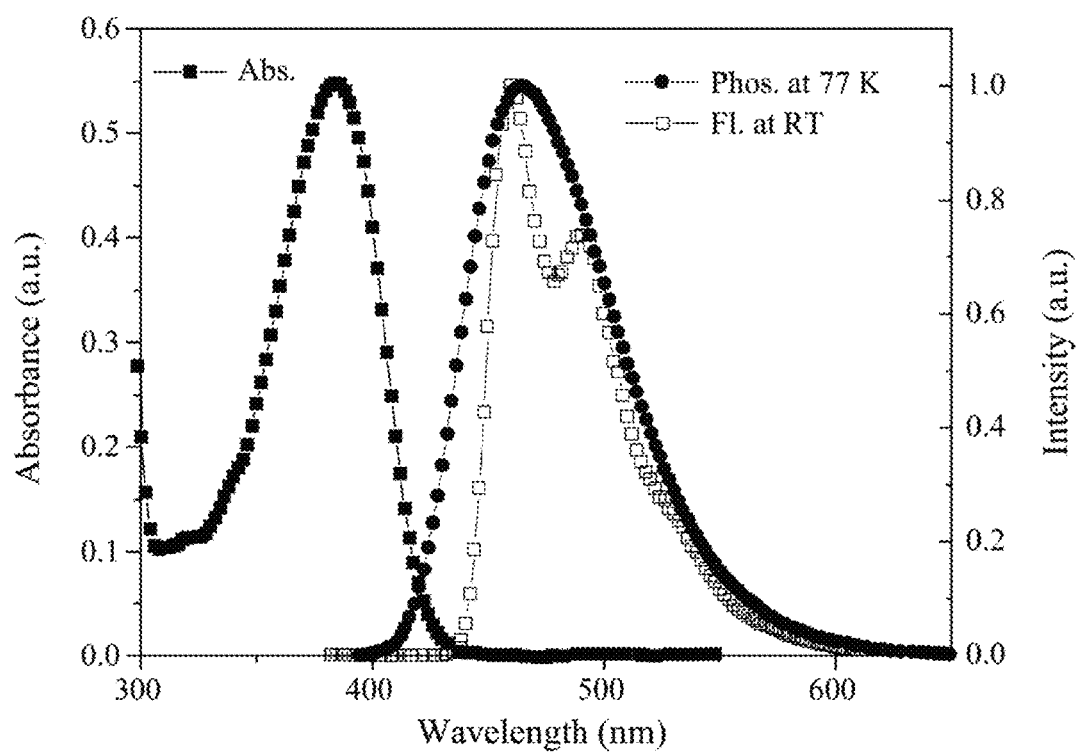
FIG. 13 shows an Abs. spectrum, a Fl. spectrum and a Phos. spectrum of Ex. 7.

FIG. 11 shows Abs. spectra, Fl. spectra and Phos. spectra of Ex. 1 and Ex. 2. FIG. 12 shows an Abs. spectrum, a Fl. spectrum and a Phos. spectrum of Ex. 6. FIG. 13 shows an Abs. spectrum, a Fl. spectrum and a Phos. spectrum of Ex. 7. The Abs. spectra and the Fl. spectrum are measured in toluene ($10^{-5}$ M) at room temperature (300 K). The Phos. spectra are measured in toluene ($10^{-5}$ M) at 77 K. The wavelength correspondent to the absorption peak, the wavelength correspondent to the fluorescence peak, and the wavelength correspondent to the phosphorescence peak of Ex. 1, Ex. 2, Ex. 6 and Ex. 7 can be observed from FIG. 11 to FIG. 13, and are recorded in Table 2.

Table 2 shows the photophysical properties of Ex. 1 to Ex. 7, wherein $\lambda_{abs}$ represents the wavelength correspondent to the absorption peak, $\lambda_{em1}$ represents the wavelength correspondent to the fluorescence peak, $\lambda_{em2}$ represents the wavelength correspondent to the phosphorescence peak, $E_S$ is the energy level of the singlet excited state, $E_T$ is the energy level of the triplet excited state, $\Delta E_{ST}=E_S-E_T$. Es can be calculated from the Fl. spectrum. $E_T$ can be calculated from the Phos. spectrum.

TABLE 2

| Ex. | $\lambda_{abs}$ (nm) | $\lambda_{em1}$ (nm) | $\lambda_{em2}$ (nm) | $E_S$ (eV) | $E_T$ (eV) | $\Delta E_{ST}$ (nm) |
|---|---|---|---|---|---|---|
| 1 | 311, 400 | 490 | 495 | 2.87 | 2.84 | 0.03 |
| 2 | 320, 418 | 508 | 509 | 2.74 | 2.70 | 0.04 |
| 3 | 334, 364 | 468 | 467 | 3.0 | 2.95 | 0.05 |
| 4 | 342, 390 | 496 | 477 | 2.87 | 2.86 | 0.01 |
| 5 | 343, 374 | 492 | 467 | 2.98 | 2.93 | 0.05 |
| 6 | 381 | 479 | 462 | 2.91 | 2.79 | 0.12 |
| 7 | 384 | 464 | 460 | 2.96 | 2.81 | 0.15 |

The thermal decomposition temperatures (Tds) of Ex. 1 to Ex. 7 are measured with thermal gravimetric analysis (TGA), and the voltammograms of Ex. 1 to Ex. 7 are obtained by cyclic voltammetry, from which the HOMO levels and the LUMO levels of Ex. 1 to Ex. 7 can be calculated. The Tds, the HOMO levels and the LUMO levels of Ex. 1 to Ex. 7 are listed in Table 3.

TABLE 3

| Ex. | Td (° C.) | HOMO (eV) | LUMO (eV) |
|---|---|---|---|
| 1 | 382 | -5.75 | -2.88 |
| 2 | 412 | -5.61 | -2.87 |
| 3 | 390 | -5.72 | -2.72 |
| 4 | 381 | -5.67 | -2.80 |
| 5 | 327 | -5.63 | -2.65 |
| 6 | 445 | -5.69 | -2.78 |
| 7 | 484 | -5.72 | -2.76 |

Figure 14:
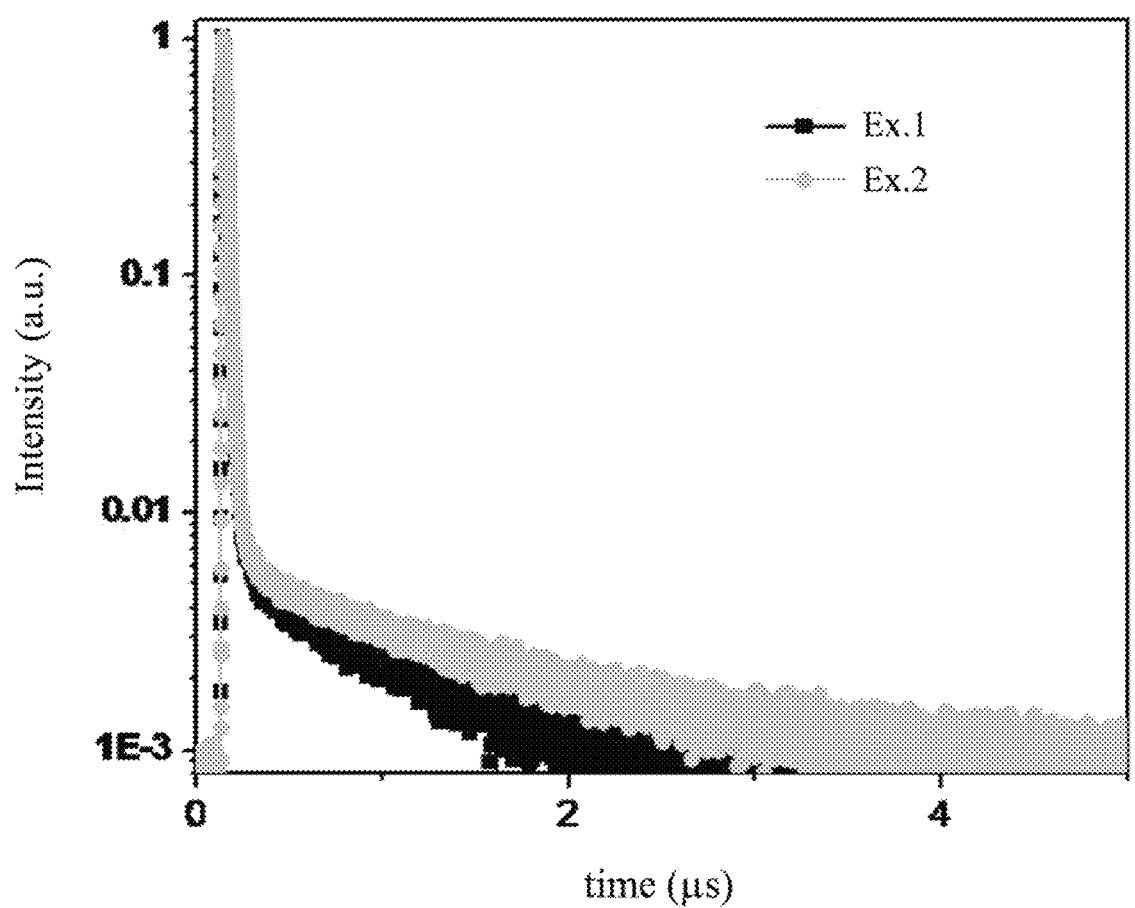
FIG. 14 is a diagram showing transient photoluminescence characteristics of Ex. 1 and Ex. 2.
Figure 15:
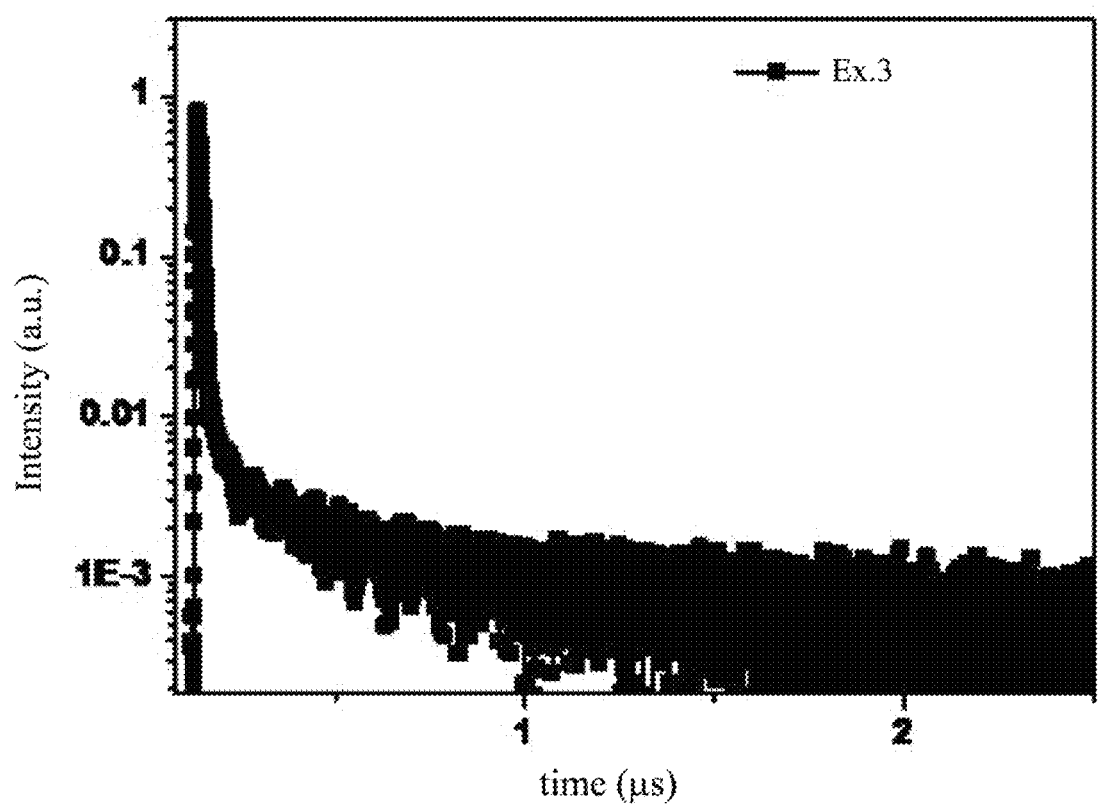
FIG. 15 is a diagram showing transient photoluminescence characteristics of Ex. 3.
Figure 16:
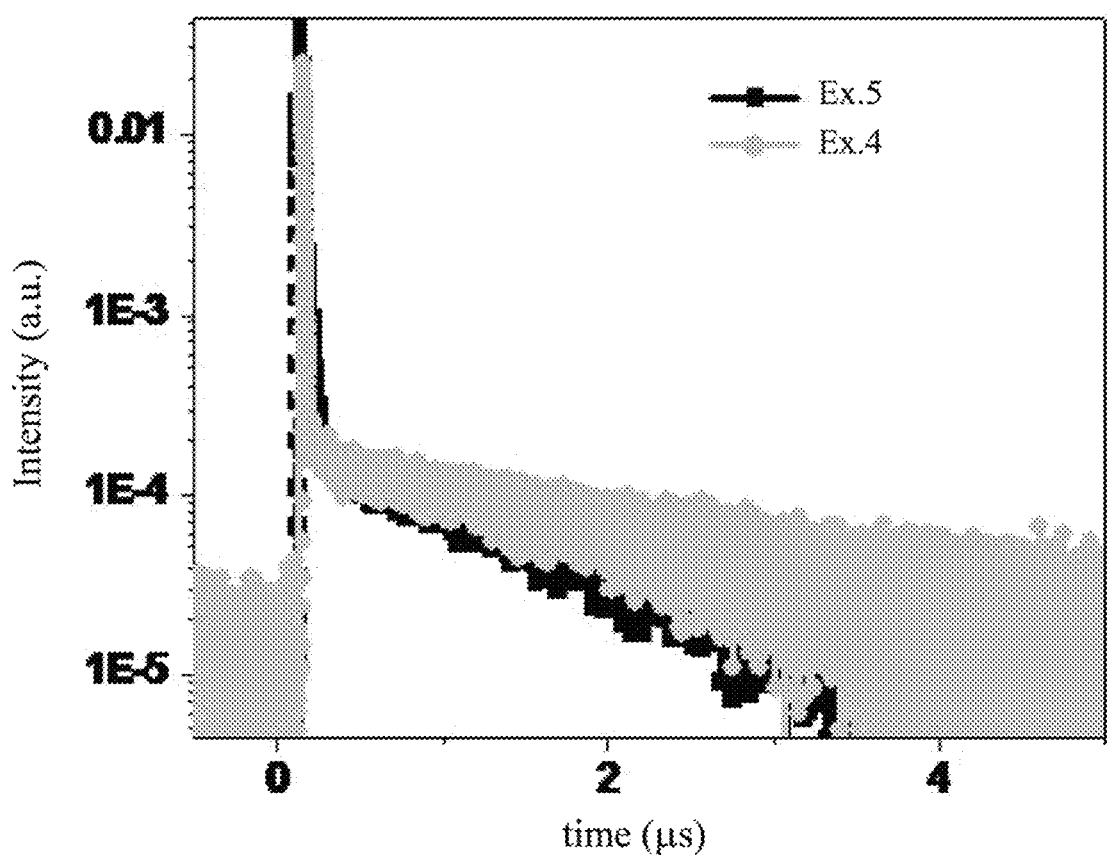
FIG. 16 is a diagram showing transient photoluminescence characteristics of Ex. 4 and Ex. 5.

FIG. 14 is a diagram showing transient photoluminescence characteristics of Ex. 1 and Ex. 2. FIG. 15 is a diagram showing transient photoluminescence characteristics of Ex. 3. FIG. 16 is a diagram showing transient photoluminescence characteristics of Ex. 4 and Ex. 5. FIGS. 14-16 are measured in toluene ($10^{-5}$ M) at room temperature under vacuum. From FIG. 14, it can be calculated that the lifetime of fluorescence ($\tau 1$) of Ex. 1 is 15 ns, the lifetime of delayed fluorescence ($\tau 2$) of Ex. 1 is 0.6 µs, the $\tau 1$ of Ex. 2 is 18 ns, and the $\tau 2$ of Ex. 2 is 1 µs. From FIG. 15, it can be calculated that the $\tau 1$ of Ex. 3 is 6.2 ns, and the $\tau 2$ of Ex. 3 is 0.2 ps. From FIG. 16, it can be calculated that the $\tau 1$ of Ex. 4 is 6.6 ns, the $\tau 2$ of Ex. 4 is 1.9 µs, the $\tau 1$ of Ex. 5 is 8.9 ns, and the $\tau 2$ of Ex. 5 is 1.3 µs.

<OLED Devices Using Examples and Comparative Examples>

OLED device A: the compound of Ex. 1 is used as a dopant of an emitting layer of the OLED A, and a doping concentration thereof is 5% (in weight percentage). The OLED device A sequentially includes an anode, a hole injection layer, a hole-transporting layer, the emitting layer, an exciton blocker, an electron-transporting layer, an electron injection layer, and a cathode. The structure of the OLED device A can refer to FIG. 3. The material and thickness of each layer of the OLED device A are as follows: ITO/NPB (30 nm)/mCP (20 nm)/CzPS:DCBPy (5%) (30 nm)/DPEPO (5 nm)/TmPyPb (60 nm)/LiF (1 nm)/Al (100 nm).

OLED device B: the compound of Ex. 2 is used as a dopant of an emitting layer of the OLED B, and a doping concentration thereof is 5% (in weight percentage). The OLED device B sequentially includes an anode, a hole injection layer, a hole-transporting layer, the emitting layer, an exciton blocker, an electron-transporting layer, an electron injection layer, and a cathode. The structure of the OLED device B can refer to FIG. 3. The material and thickness of each layer of the OLED device B are as follows: ITO/NPB (30 nm)/TAPC (20 nm)/CBP:DTCBPy (5%) (30 nm)/PPT (10 nm)/TmPyPb (55 nm)/LiF(1 nm)/Al (100 nm).

OLED device C: the compound of Ex. 3 is used as a dopant of an emitting layer of the OLED C, and a doping concentration thereof is 5% (in weight percentage). The OLED device C sequentially includes an anode, a hole injection layer, a hole-transporting layer, the emitting layer, an exciton blocker, an electron-transporting layer, an electron injection layer, and a cathode. The structure of the OLED device C can refer to FIG. 3. The material and thickness of each layer of the OLED device C are as follows: ITO/NPB (30 nm)/mCP (20 nm)/DPEPO:mDCBPy(5%)(30 nm)/PPT (5 nm)/TmPyPb (60 nm)/LiF(1 nm)/Al (100 nm).

OLED device D: the compound of Ex. 4 is used as a dopant of an emitting layer of the OLED D, and a doping concentration thereof is 7% (in weight percentage). The OLED device D sequentially includes an anode, a hole injection layer, a hole-transporting layer, the emitting layer, an exciton blocker, an electron-transporting layer, an electron injection layer, and a cathode. The structure of the OLED device D can refer to FIG. 3. The material and thickness of each layer of the OLED device D are as follows: ITO/NPB (30 nm)/TAPC (20 nm)/mCBP:mDTCBPy (7%) (30 nm)/DPEPO (5 nm)/TmPyPb (60 nm)/LiF (0.8 nm)/Al (100 nm).

OLED device E: the compound of Ex. 5 is used as a dopant of an emitting layer of the OLED E, and a doping concentration thereof is 5% (in weight percentage). The OLED device E sequentially includes an anode, a hole injection layer, a hole-transporting layer, the emitting layer, an exciton blocker, an electron-transporting layer, an electron injection layer, and a cathode. The structure of the OLED device E can refer to FIG. 3. The material and thickness of each layer of the OLED device E are as follows: ITO/NPB (30 nm)/mCP (20 nm)/mCBP:mTCBPy (5%) (30 nm)/DPEPO (5 nm)/TmPyPb (60 nm)/LiF (0.8 nm)/Al (100 nm).

OLED device F: the compound of Ex. 6 is used as a dopant of an emitting layer of the OLED F, and a doping concentration thereof is 7% (in weight percentage). The OLED device F sequentially includes an anode, a hole injection layer, a hole-transporting layer, the emitting layer, an exciton blocker, an electron-transporting layer, an electron injection layer, and a cathode. The structure of the OLED device F can refer to FIG. 3. The material and thickness of each layer of the OLED device F are as follows:

ITO/NPB (30 nm)/TAPC (20 nm)/mCBP:3BP-pTC (7%)(30 nm)/PPT (10 nm)/TmPyPb (55 nm)/LiF (0.8 nm)/Al (100 nm).

OLED device G: the compound of Ex. 7 is used as a dopant of an emitting layer of the OLED G, and a doping concentration thereof is 7% (in weight percentage). The OLED device G sequentially includes an anode, a hole injection layer, a hole-transporting layer, the emitting layer, an exciton blocker, an electron-transporting layer, an electron injection layer, and a cathode. The structure of the OLED device G can refer to FIG. 3. The material and thickness of each layer of the OLED device G are as follows: ITO/NPB (30 nm)/TAPC (20 nm)/mCBP:3BP-pDTC (7%) (30 nm)/DPEPO (5 nm)/TmPyPb (65 nm)/LiF (0.8 nm)/Al (100 nm).

OLED device H: the compound of Comparative Ex. 1 is used as a dopant of an emitting layer of the OLED H, and a doping concentration thereof is 7% (in weight percentage). The OLED device H sequentially includes an anode, a hole injection layer, a hole-transporting layer, the emitting layer, an exciton blocker, an electron-transporting layer, an electron injection layer, and a cathode. The structure of the OLED device H can refer to FIG. 3. The material and thickness of each layer of the OLED device H are as follows: ITO/NPB (30 nm)/TAPC (20 nm)/mCBP:DCPKPy (7%) (30 nm)/DPEPO (5 nm)/TmPyPb (60 nm)/LiF (0.8 nm)/Al (100 nm).

The structures of the compounds used in the OLED device A to the OLED device H are as follows.

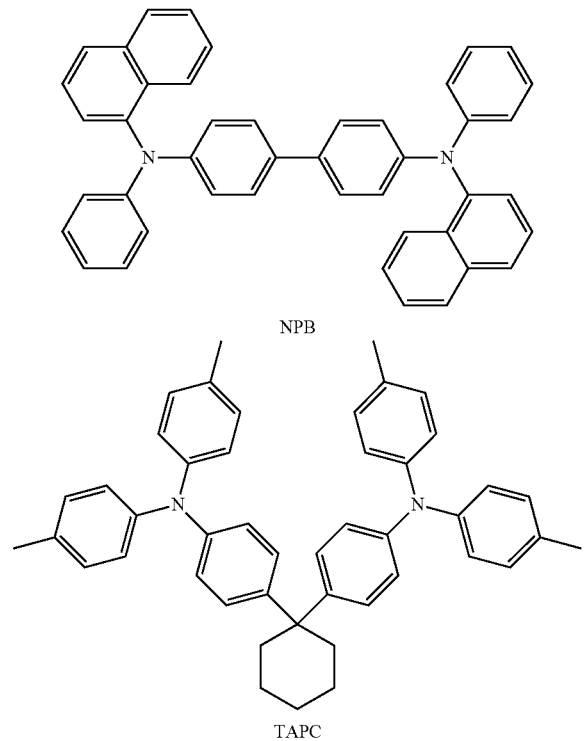

NPB

TAPC

-continued

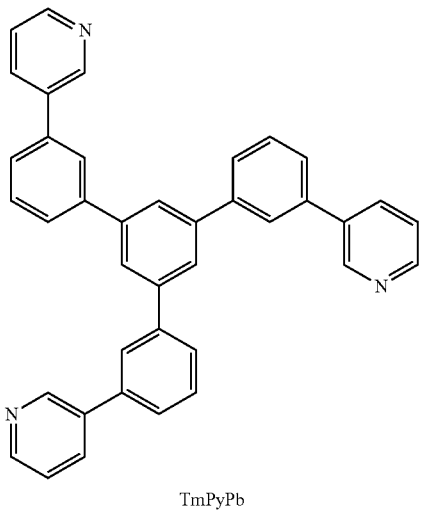

TmPyPb

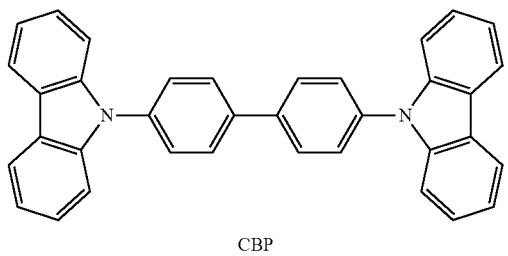

CBP

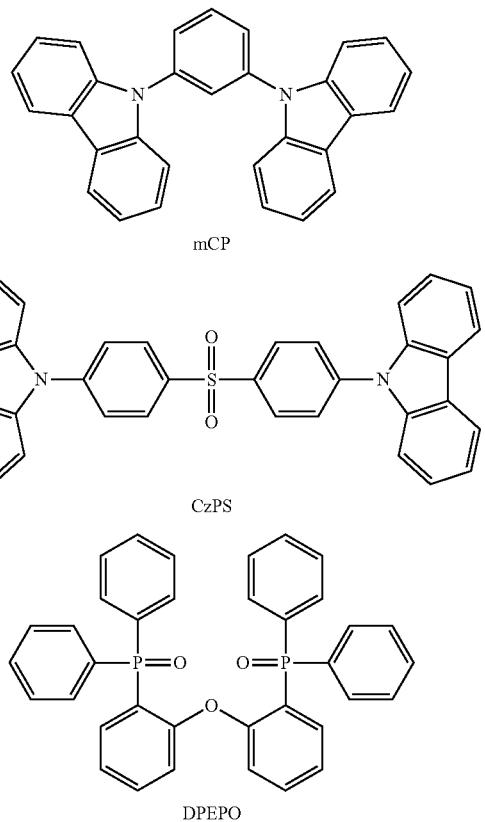

mCP

CzPS

DPEPO

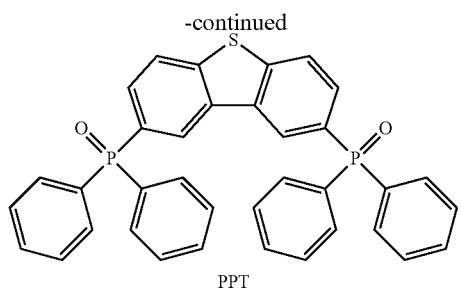

PPT

Figure 17:
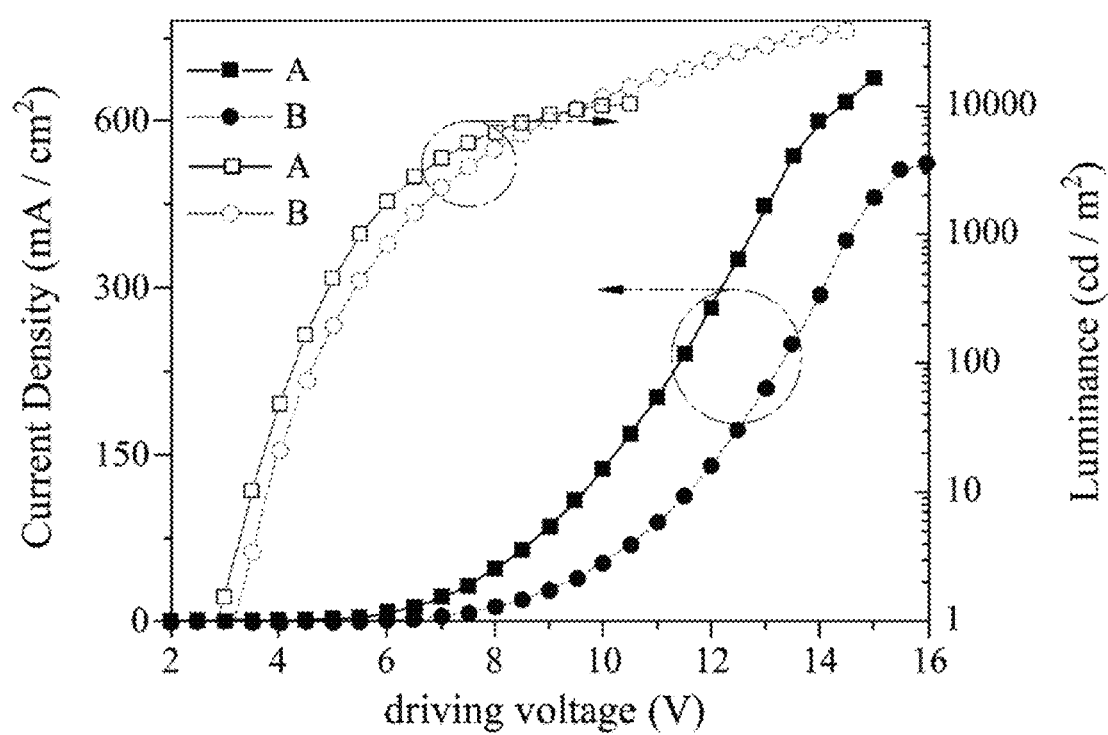
FIG. 17 shows relationships of current density, luminance and driving voltage of an OLED device A and an OLED device B.
Figure 18:
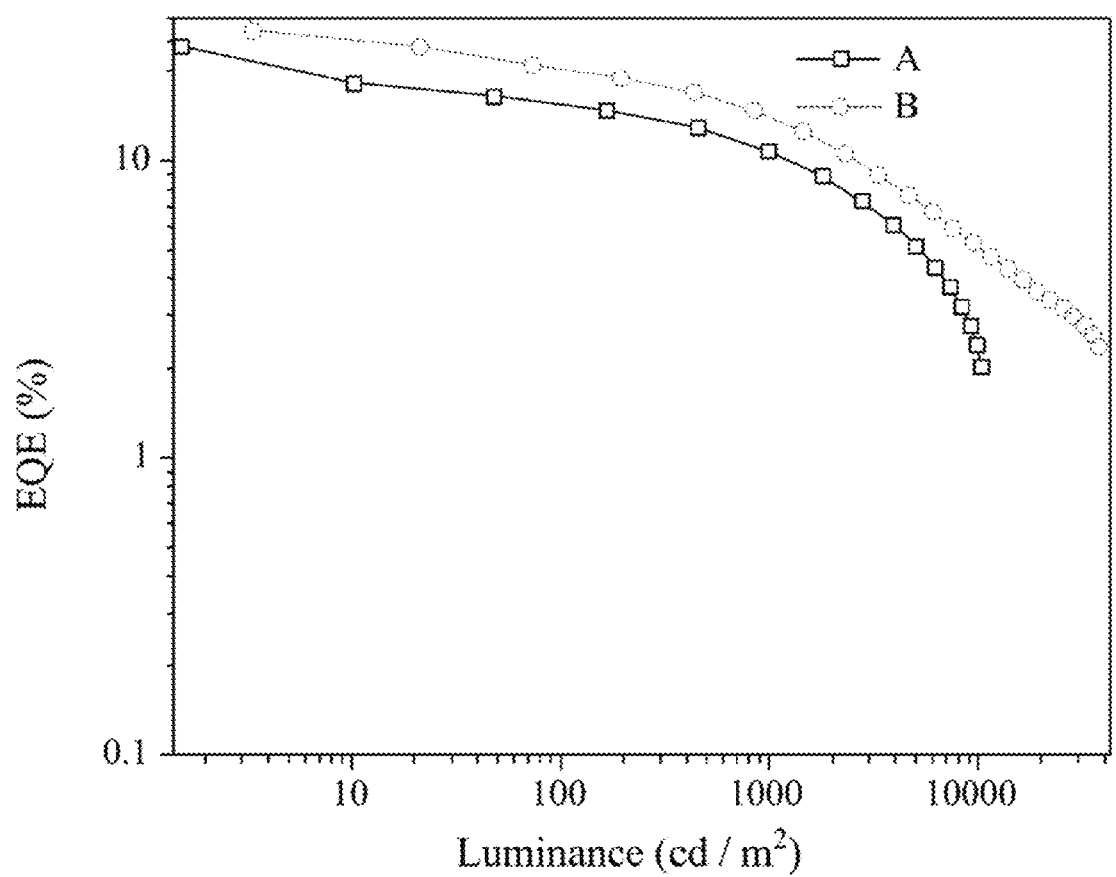
FIG. 18 shows relationships of EQE and luminance of the OLED device A and the OLED device B.
Figure 19:
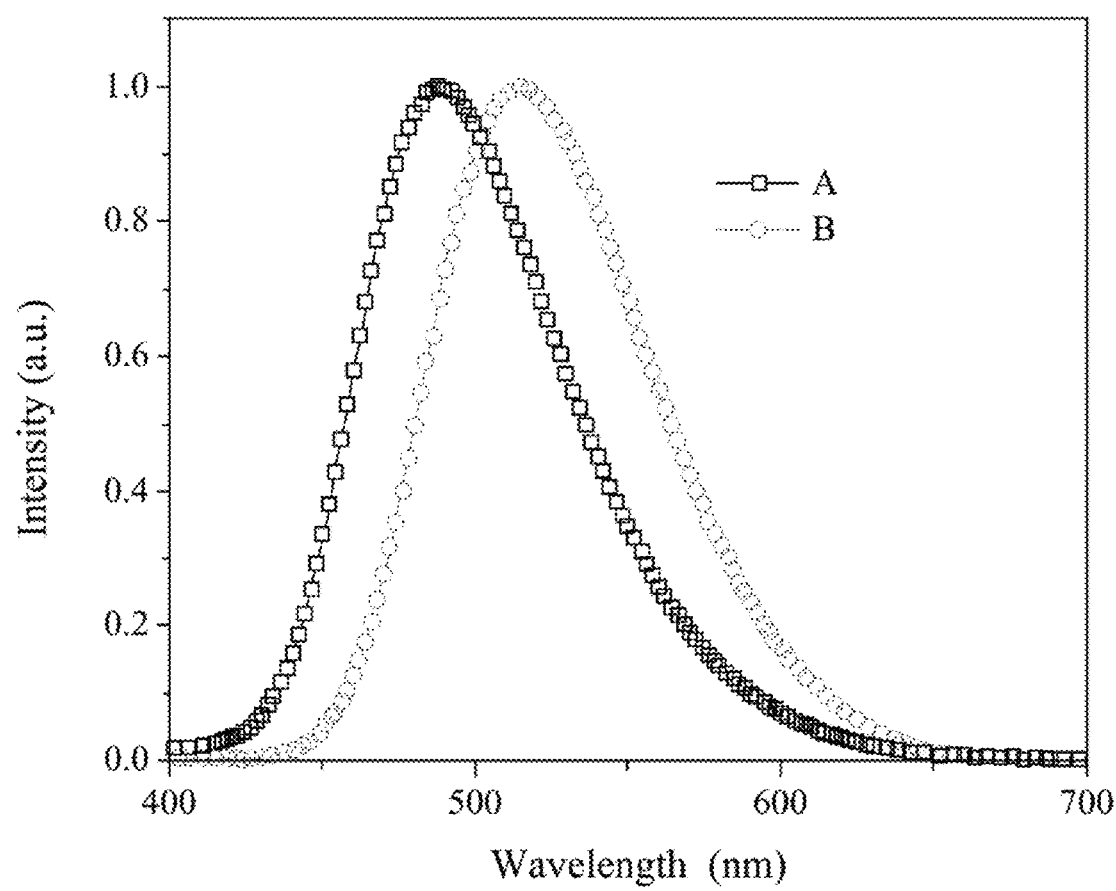
FIG. 19 shows photoluminescence spectra of the OLED device A and the OLED device B.
Figure 20:
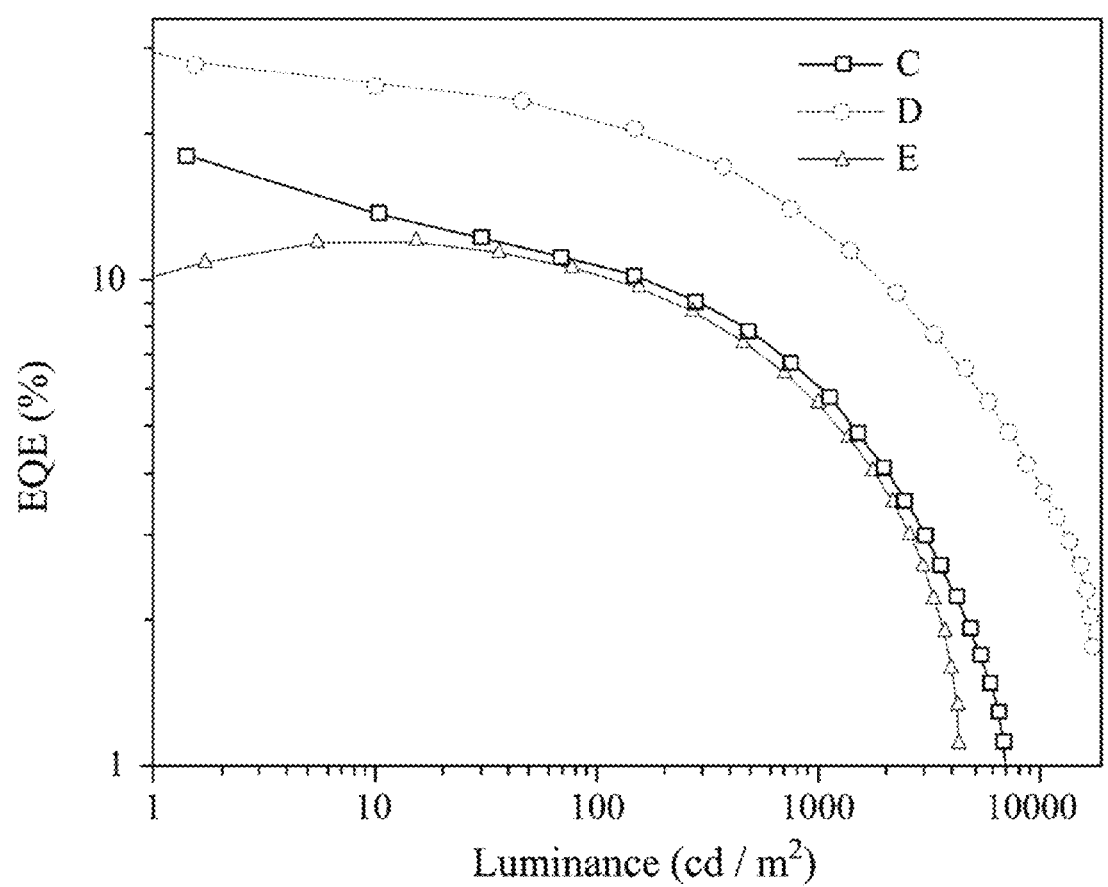
FIG. 20 shows relationships of EQE and luminance of an OLED device C, an OLED device D and an OLED device E.
Figure 21:
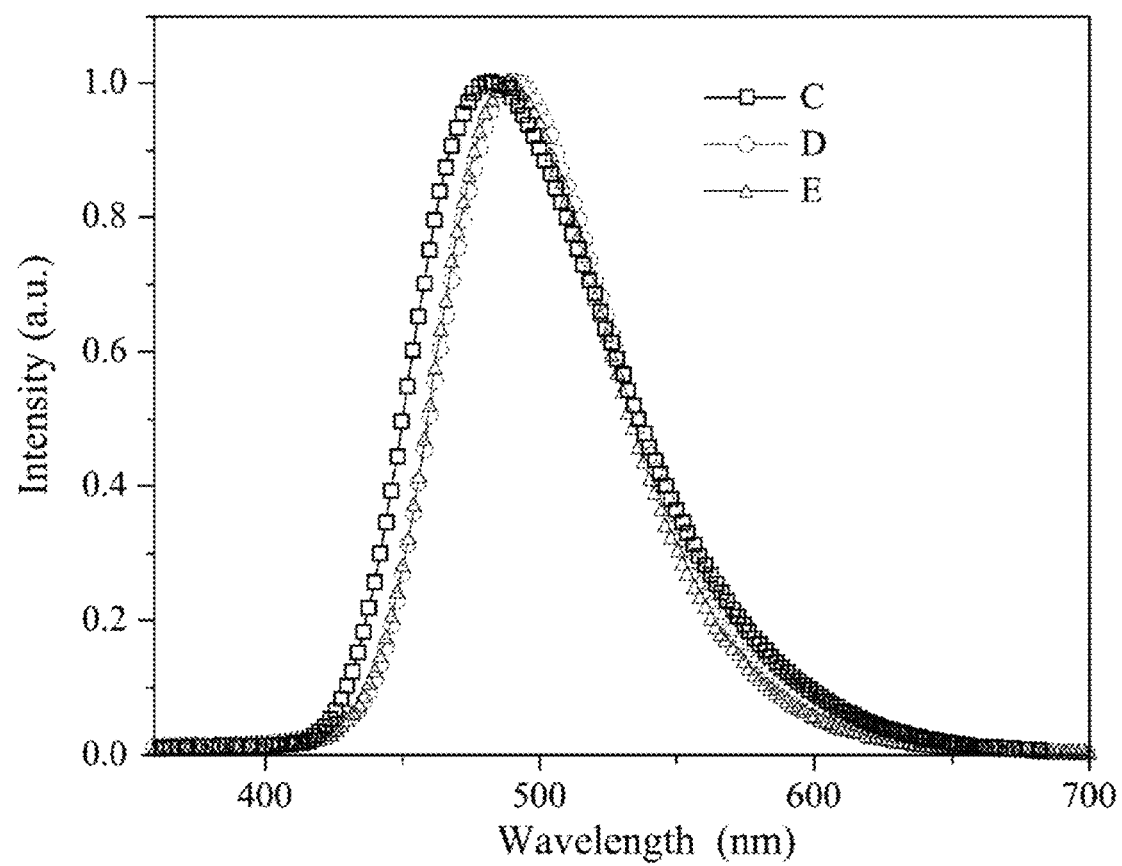
FIG. 21 shows photoluminescence spectra of the OLED device C, the OLED device D and the OLED device E.
Figure 22:
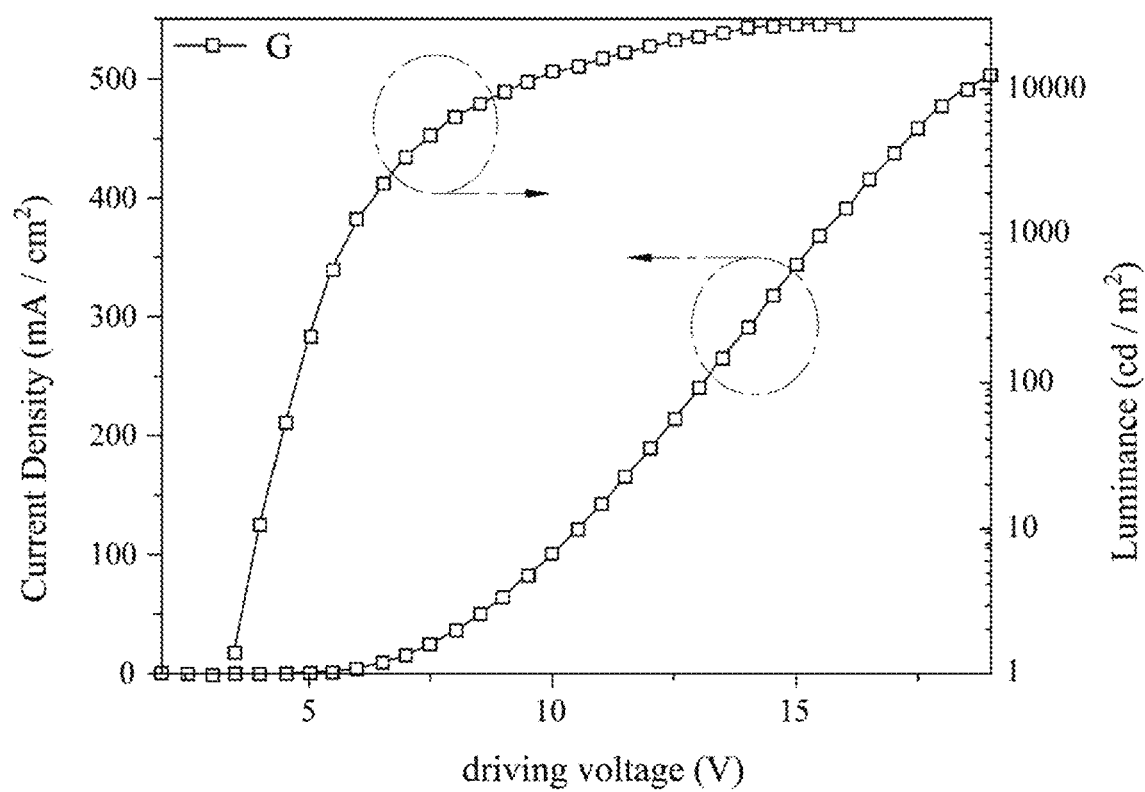
FIG. 22 shows relationships of current density, luminance and driving voltage of an OLED device G.
Figure 23:
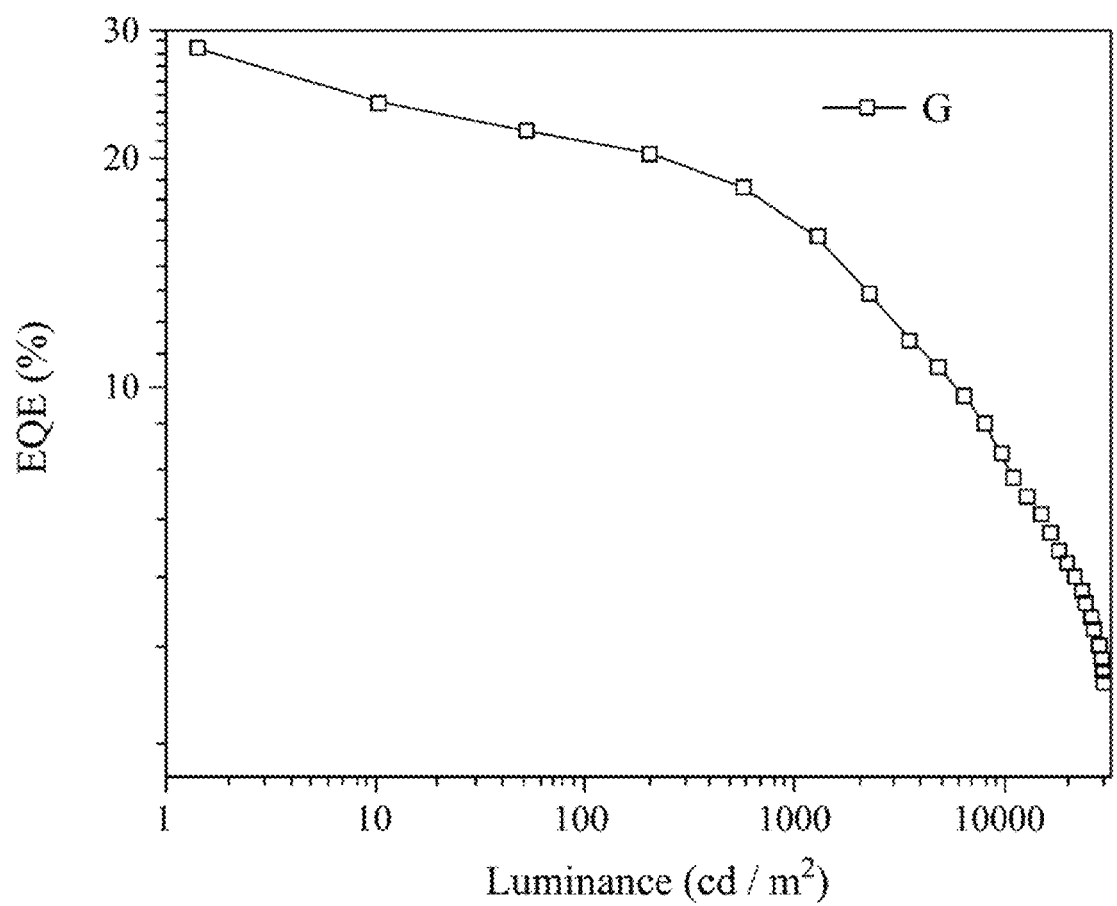
FIG. 23 shows a relationship of EQE and luminance of the OLED device G.
Figure 24:
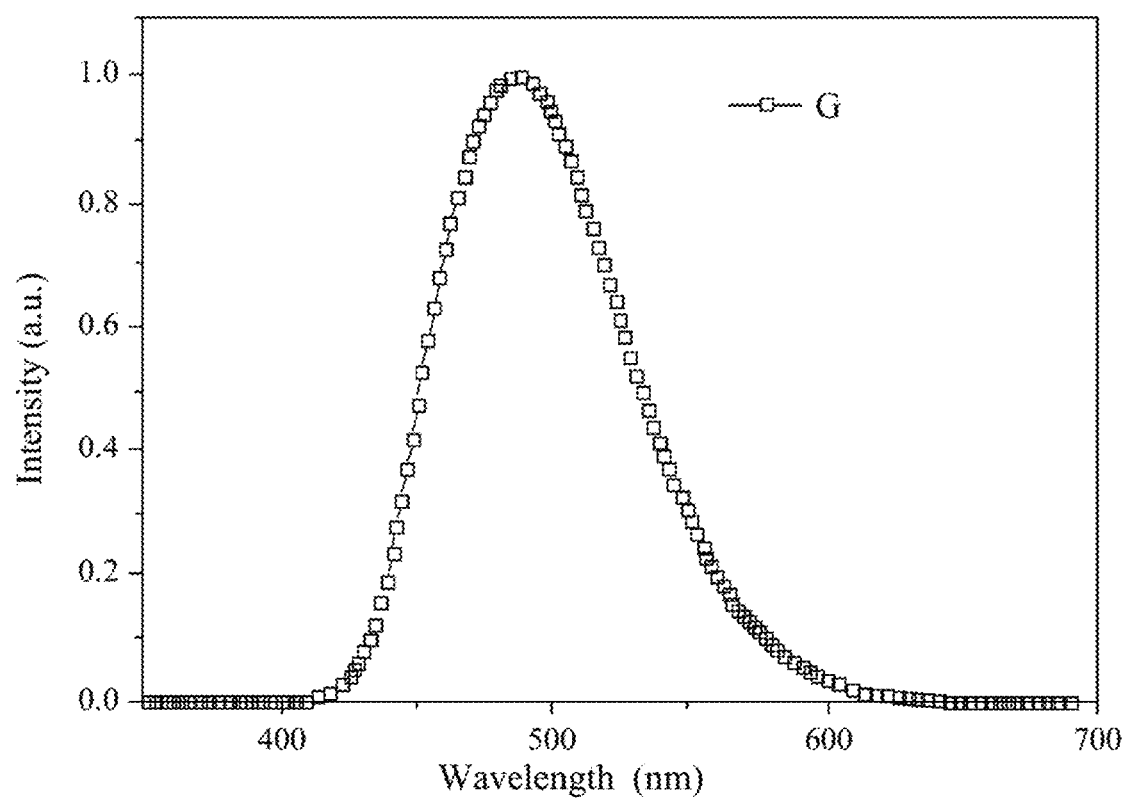
FIG. 24 shows photoluminescence spectrum of the OLED device G.
Figure 25:
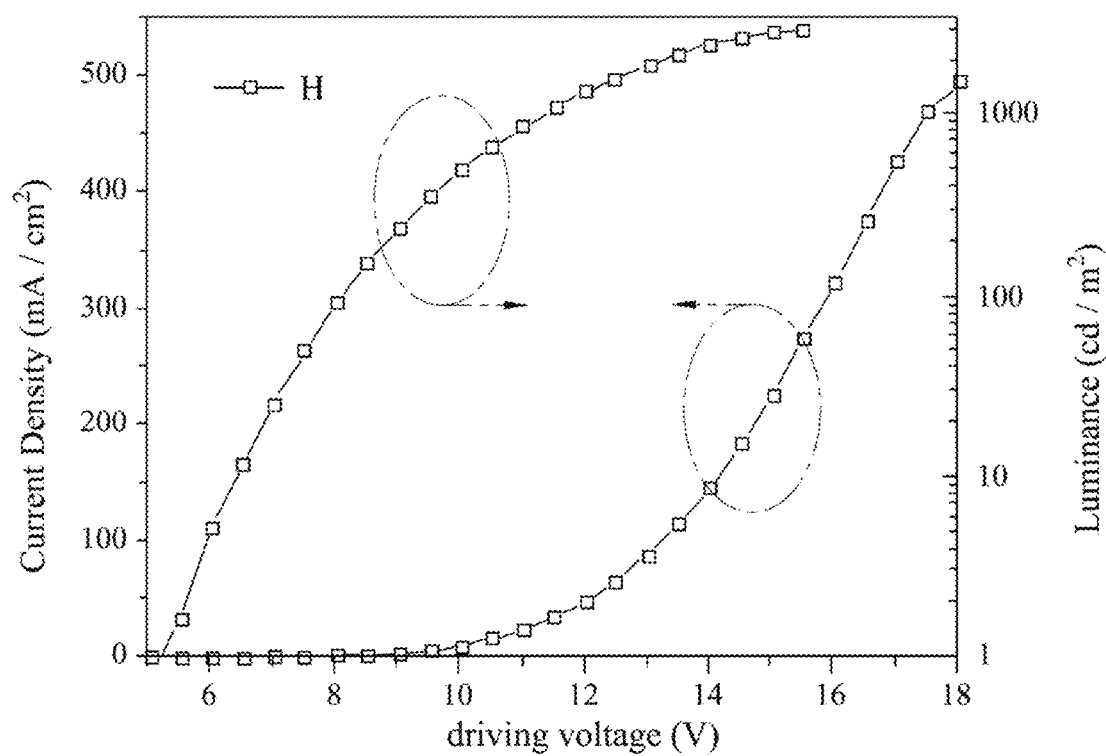
FIG. 25 shows relationships of current density, luminance and driving voltage of an OLED device H.
Figure 26:
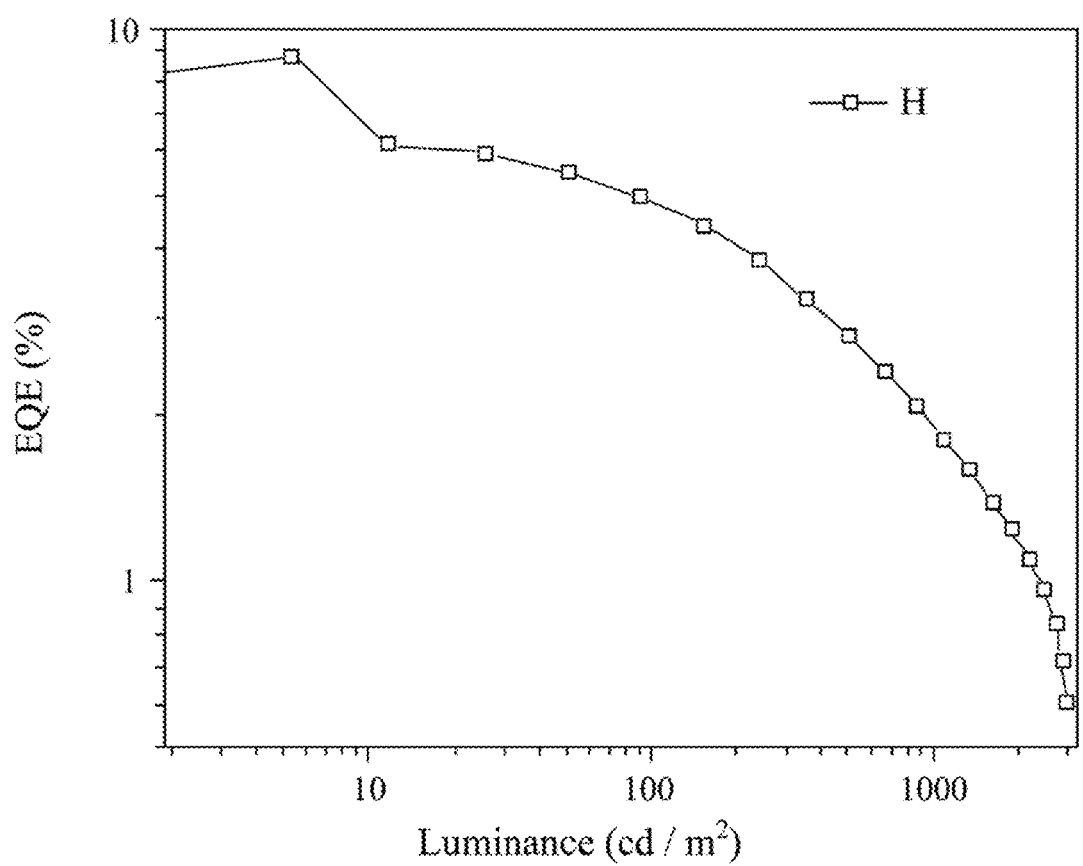
FIG. 26 shows a relationship of EQE and luminance of the OLED device H.
Figure 27:
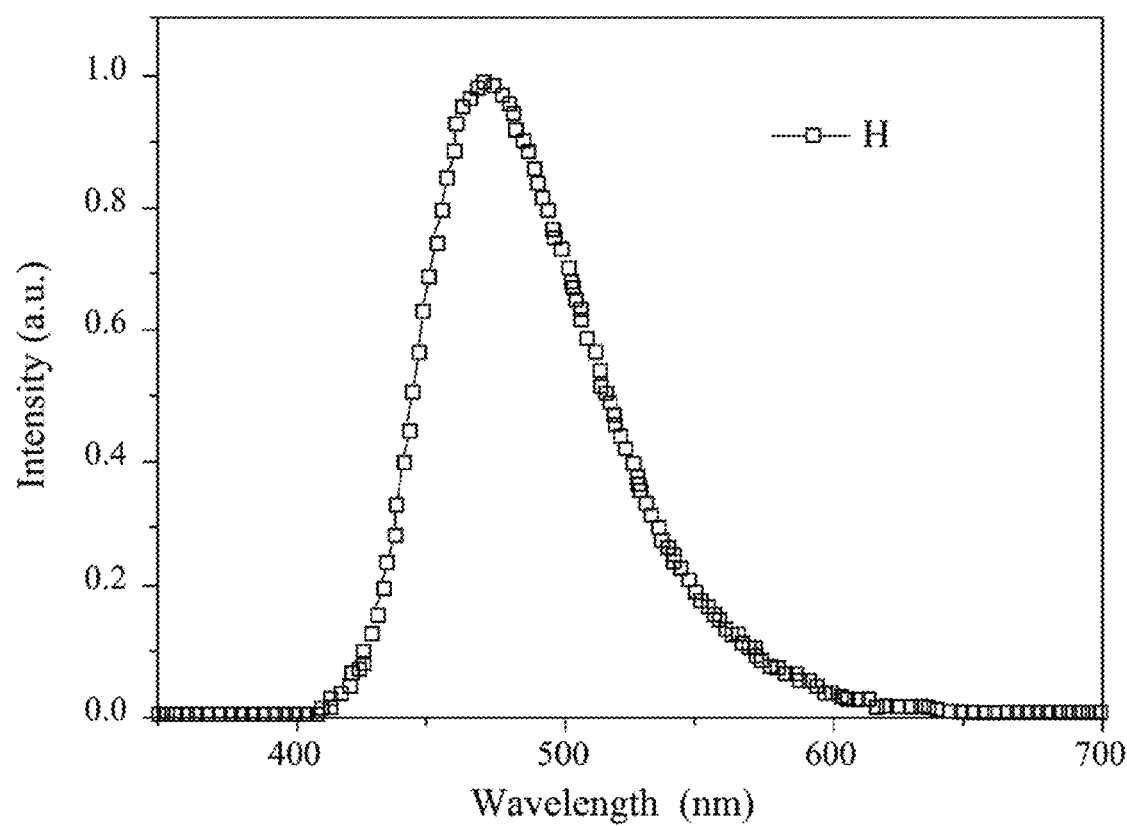
FIG. 27 shows photoluminescence spectrum of the OLED device H.

The properties of the OLED device A to OLED device H can refer to FIGS. 17-24. FIG. 17 shows relationships of current density, luminance and driving voltage of the OLED device A and the OLED device B. FIG. 18 shows relationships of EQE and luminance of the OLED device A and the OLED device B. FIG. 19 shows photoluminescence spectra of the OLED device A and the OLED device B. FIG. 20 shows relationships of EQE and luminance of the OLED device C, the OLED device D and the OLED device E. FIG. 21 shows photoluminescence spectra of the OLED device C, the OLED device D and the OLED device E. FIG. 22 shows relationships of current density, luminance and driving voltage of the OLED device G. FIG. 23 shows a relationship of EQE and luminance of the OLED device G. FIG. 24 shows photoluminescence spectrum of the OLED device G. FIG. 25 shows relationships of current density, luminance and driving voltage of the OLED device H. FIG. 26 shows a relationship of EQE and luminance of the OLED device H. FIG. 27 shows photoluminescence spectrum of the OLED device H. The turn on voltage (Vd), the maximum EQE (EQE), the maximum current density (CD), the maximum luminance (L), the maximum current efficiency (CE), the maximum power efficiency (PE) and the chromaticity coordinate (CIE) of each of the OLED device A to OLED device H are listed in Table 4 and Table 5.

TABLE 4

| OLED device | Vd (V) | EQE (%) | CD (mA/cm²) | L (Cd/m²) | CE (Cd/A) | PE (lm/W) |
|---|---|---|---|---|---|---|
| A | 2.8 | 24.0 | 651 | 10300 | 54.7 | 57.2 |
| B | 3.1 | 27.2 | 519 | 37700 | 94.6 | 84.5 |
| C | 2.8 | 18.0 | 583 | 7000 | 41.3 | 43.1 |
| D | 3.3 | 28.1 | 520 | 17000 | 67.0 | 60.1 |
| E | 5.2 | 12.2 | 464 | 4332 | 25.0 | 14.2 |
| F | 3.5 | 14.9 | 737 | 10799 | 32.3 | 25.2 |
| G | 3.5 | 27.0 | 507 | 12961 | 58.1 | 40.7 |
| H | 5.1 | 8.8 | 492 | 2900 | 15.3 | 8.1 |

TABLE 5

| | OLED device | | | |
|---|---|---|---|---|
| | A | B | C | D |
| CIE (x, y) | (0.17, 0.36) | (0.30, 0.64) | (0.18, 0.32) | (0.17; 0.37) |

| | OLED device | | | |
|---|---|---|---|---|
| | E | F | G | H |
| CIE (x, y) | (0.16, 0.36) | (0.17, 0.31) | (0.15, 0.31) | (0.15; 0.22) |

As shown in Table 4, when the compounds according to the present disclosure are used as the dopants in the emitting layers of the OLED device A to the OLED device G, the OLED device A to the OLED device G are featured with excellent efficiency. For example, the maximum EQEs of the OLED device A to the OLED device G are all greater than 12.2%. In contrast, the maximum EQE of the OLED device H used the comparative Ex. 1 can only reach to 8.8%. The main difference between the compound of the comparative Ex. 1 and the compounds according to the present disclosure is the electron accepting group. There are one more phenyl group and one more ketone group in the electron accepting group of the compound of the comparative Ex. 1. From the results shown in Table 4, it is known that the structure of the TADF material is critical to the performance of the OLED devices. By improving the molecular structure, the compound according to the present disclosure indeed enhance the efficiency of OLED device.

Moreover, as shown in Table 5, the blue OLED device can be provided by using the compound according to the present disclosure, which overcomes the disadvantage of the phosphorescence materials and can provide a wide light color tenability.

Figure 28:
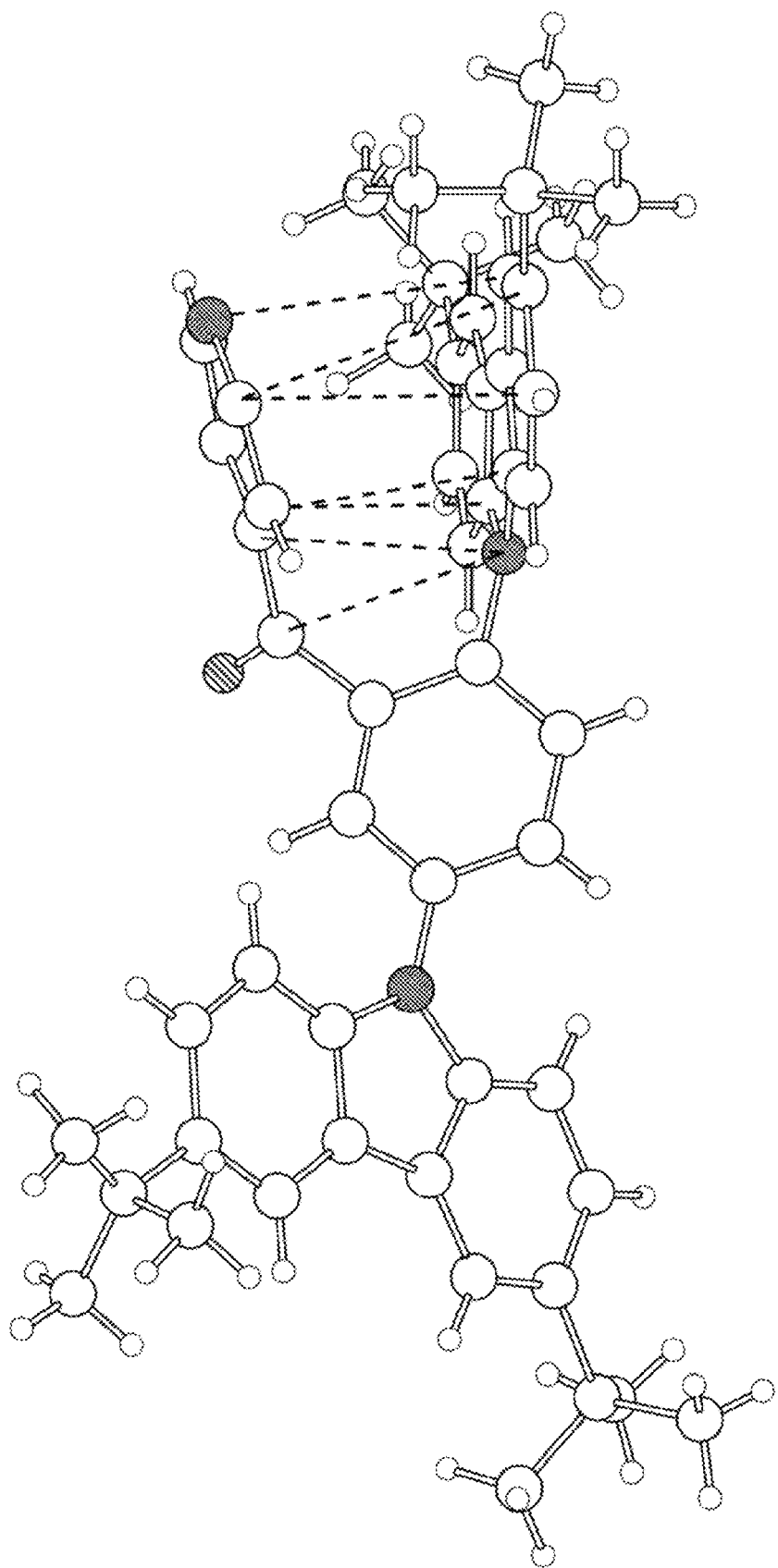
FIG. 28 shows a single-crystal X-ray diffraction result of Ex. 2.

FIG. 28 shows a single-crystal X-ray diffraction result of Ex. 2. As shown in FIG. 28, the compound of Ex. 2 includes two 3,6-di-t-butyl-carbazole groups, which are located at the ortho position and the meta position in respect to the ketone group, and there is a strong intramolecular space interaction between the ortho 3,6-di-t-butyl-carbazole group and the pyridyl group of the electron accepting group. A distance between the ortho 3,6-di-t-butyl-carbazole group and the pyridyl group of the electron accepting group is about 2.9 Å to 3.7 Å, the ΔEst can be further reduced thereby, and the probability of RISC can be enhanced. Accordingly, the efficiency of the OLED can be further enhanced.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A compound, comprising a structure of Formula (I):

wherein $A^1$ is a pyridyl group, $A^2$ is a phenyl group or a pyridyl group, and hydrogens of the $A^1$ are both unsubstituted or substituted by a structure of Formula (i), Formula (ii) or Formula (iii), and at least one of hydrogens of the $A^2$ is substituted by the structure of Formula (i), Formula (ii) or Formula (iii):

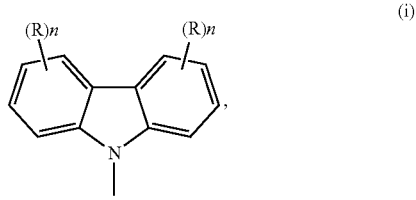

-continued

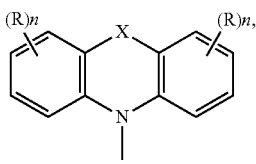
(ii)

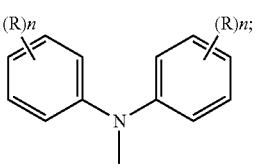
(iii)

wherein n is independently an integer of 0 to 4, R is independently a monovalent group having 1 to 60 carbon atoms, X is —$NR^{14}$—, —S— or —$CR^{15}R^{16}$—, and $R^{14}$, $R^{15}$ and $R^{16}$ are independently —H, an alkyl group or an aryl group.

2. The compound of claim 1, wherein the compound comprises a structure of Formula (I-1):

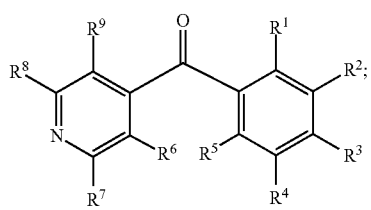
(I-1)

wherein $R^1$, $R^2$, $R^3$, $R^4$ and $R^5$ are independently —H, the structure of Formula (i), the structure of Formula (ii) or the structure of Formula (iii), at least one of the $R^1$, $R^2$, $R^3$, $R^4$ and $R^5$ is the structure of Formula (i), the structure of Formula (ii) or the structure of Formula (iii), and $R^6$, $R^7$, $R^8$ and $R^9$ are —H.

3. The compound of claim 1, wherein the compound comprises a structure of Formula (I-2):

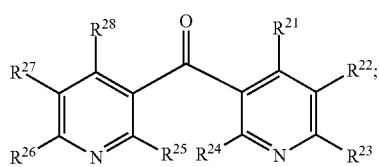
(I-2)

wherein $R^{21}$, $R^{22}$, $R^{23}$, $R^{24}$, $R^{25}$, $R^{26}$, $R^{27}$ and $R^{28}$ are independently —H, the structure of Formula (i), the structure of Formula (ii) or the structure of Formula (iii), and at least one of the $R^{21}$, $R^{22}$, $R^{23}$, $R^{24}$, $R^{25}$, $R^{26}$, $R^{27}$ and $R^{28}$ is the structure of Formula (i), the structure of Formula (ii) or the structure of Formula (iii).

4. The compound of claim 1, wherein the compound comprises a structure of Formula (I-3):

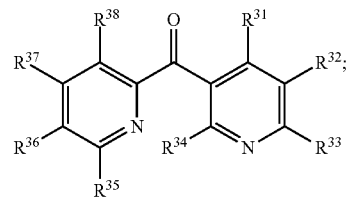
(I-3)

wherein $R^{31}$, $R^{32}$, $R^{33}$ and $R^{34}$ are independently —H, the structure of Formula (i), the structure of Formula (ii) or the structure of Formula (iii), at least one of the $R^{31}$, $R^{32}$, $R^{33}$ and $R^{34}$ is the structure of Formula (i), the structure of Formula (ii) or the structure of Formula (iii), and $R^{35}$, $R^{36}$, $R^{37}$ and $R^{38}$ are —H.

5. An emitting layer of an organic light emitting diode (OLED), comprising a dopant comprising a structure of Formula (I):

(I)

wherein $A^1$ is a pyridyl group, $A^2$ is a phenyl group or a pyridyl group, and hydrogens of the $A^1$ are both unsubstituted or substituted by a structure of Formula (i), Formula (ii) or Formula (iii), and at least one of hydrogens of the $A^2$ is substituted by the structure of Formula (i), Formula (ii) or Formula (iii):

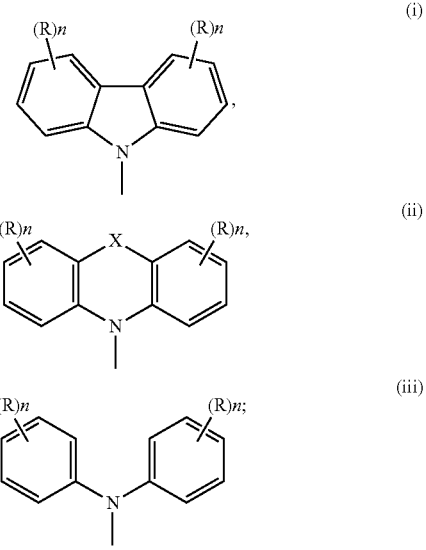

wherein n is independently an integer of 0 to 4, R is independently a monovalent group having 1 to 60 carbon atoms, X is —$NR^{14}$—, —S— or —$CR^{15}R^{16}$—, and $R^{14}$, $R^{15}$ and $R^{16}$ are independently —H, an alkyl group or an aryl group.

6. The emitting layer of the OLED of claim 5, wherein the dopant comprises a structure of Formula (I-1):

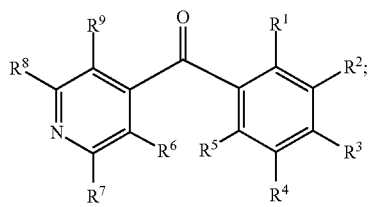

(I-1)

wherein $R^1$, $R^2$, $R^3$, $R^4$ and $R^5$ are independently —H, the structure of Formula (i), the structure of Formula (ii) or the structure of Formula (iii), at least one of the $R^1$, $R^2$, $R^3$, $R^4$ and $R^6$ is the structure of Formula (i), the structure of Formula (ii) or the structure of Formula (iii), and $R^6$, $R^7$, $R^8$ and $R^9$ are —H.

7. The emitting layer of the OLED of claim 5, wherein the dopant comprises a structure of Formula (I-2):

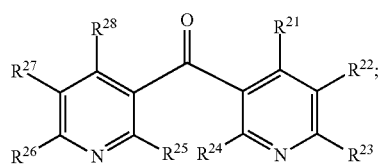

(I-2)

wherein $R^{21}$, $R^{22}$, $R^{23}$, $R^{24}$, $R^{25}$, $R^{26}$, $R^{27}$ and $R^{28}$ are independently —H, the structure of Formula (i), the structure of Formula (ii) or the structure of Formula (iii), and at least one of the $R^{21}$, $R^{22}$, $R^{23}$, $R^{24}$, $R^{25}$, $R^{26}$, $R^{27}$ and $R^{28}$ is the structure of Formula (i), the structure of Formula (ii) or the structure of Formula (iii).

8. The emitting layer of the OLED of claim 5, wherein the dopant comprises a structure of Formula (I-3):

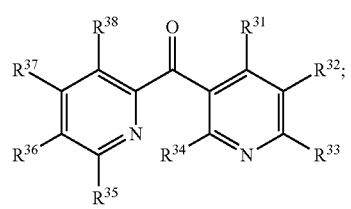

(I-3)

wherein $R^{31}$, $R^{32}$, $R^{33}$ and $R^{34}$ are independently —H, the structure of Formula (i), the structure of Formula (ii) or the structure of Formula (iii), at least one of the $R^{31}$, $R^{32}$, $R^{33}$ and $R^{34}$ is the structure of Formula (i), the structure of Formula (ii) or the structure of Formula (iii), and $R^{35}$, $R^{36}$, $R^{37}$ and $R^{38}$ are —H.

9. The emitting layer of the OLED of claim 5, further comprising:

a host material comprising any one of structures of Formula (1) to Formula (9):

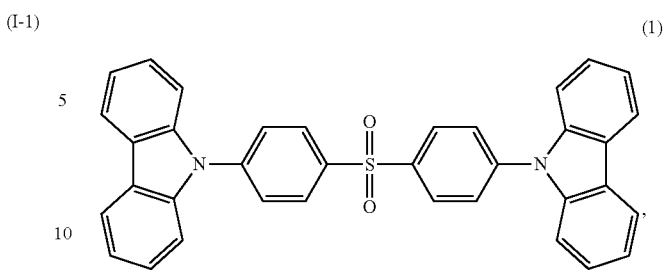

(1)

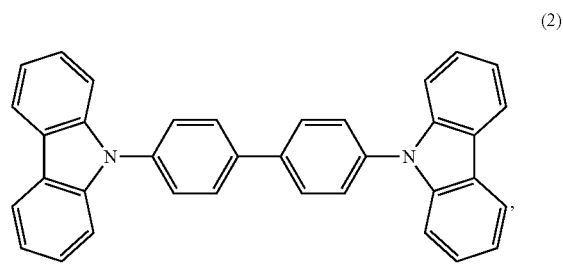

(2)

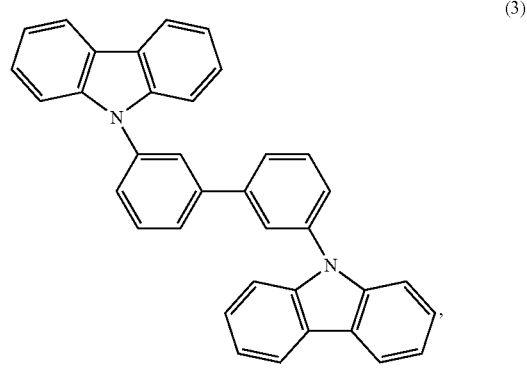

(3)

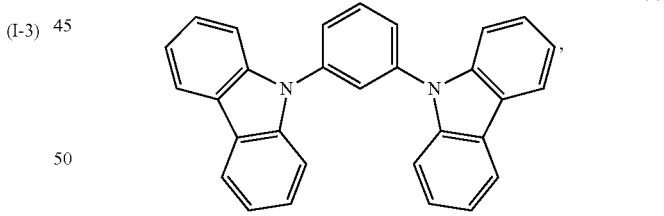

(4)

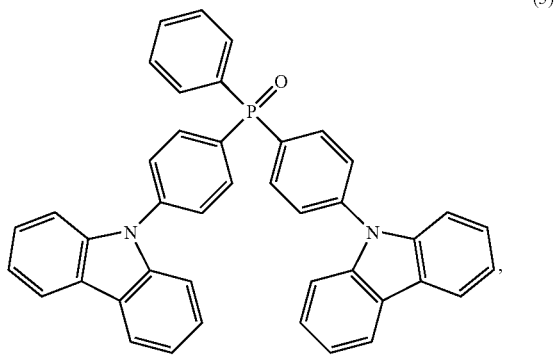

(5)

-continued
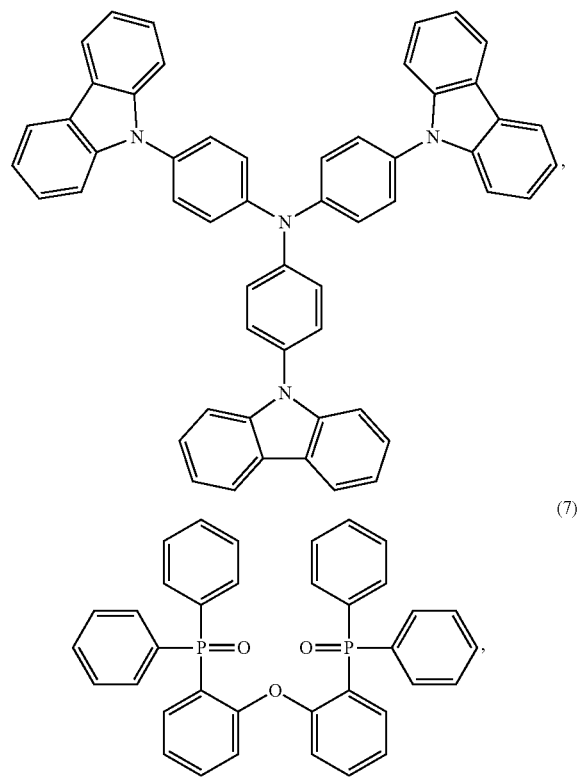
(6)
(7)
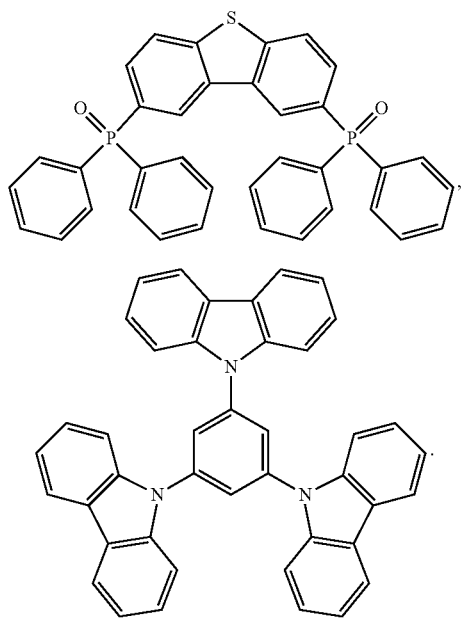
(8)
(9)
10. The emitting layer of the OLED of claim 5, wherein a doping concentration of the dopant in the emitting layer is in a range of 5 wt % to 30 wt %.
11. An OLED device, comprising:
the emitting layer of the OLED of claim 5.
* * * * *